(12) United States Patent
Smith et al.

(10) Patent No.: US 6,869,589 B1
(45) Date of Patent: Mar. 22, 2005

(54) CRYPTATE COMPOUNDS AND METHODS FOR DIAGNOSIS AND THERAPY

(75) Inventors: Suzanne V. Smith, Sylvania (AU); John M. Harrowfield, Daglish (AU); Nadine M. Di Bartolo, Sutherland (AU); Alan McLeod Sargeson, Curtin (AU)

(73) Assignees: Australian Nuclear Science & Technology Organization (AU); The Australian National University (AU)

(*) Notice: Subject to any disclaimer, the term of this patent is extended or adjusted under 35 U.S.C. 154(b) by 0 days.

(21) Appl. No.: 09/869,777

(22) PCT Filed: Jan. 5, 2000

(86) PCT No.: PCT/AU00/00003

§ 371 (c)(1),
(2), (4) Date: Sep. 21, 2001

(87) PCT Pub. No.: WO00/40585

PCT Pub. Date: Jul. 13, 2000

(30) Foreign Application Priority Data

Jan. 5, 1999 (AU) .............................................. PP 8038

(51) Int. Cl.$^7$ ........................ A61K 51/00; A61B 5/005; C07D 267/22; C07D 225/00
(52) U.S. Cl. .................. 424/1.65; 424/9.363; 424/1.69; 424/1.77; 540/465; 540/467; 540/469; 540/456
(58) Field of Search ............................... 424/1.65, 1.69, 424/1.11, 1.77, 9.363; 534/10, 11, 12, 13, 14; 540/465, 467, 469, 456

(56) References Cited

U.S. PATENT DOCUMENTS 4,741,900 A * 5/1988 Alvarez et al. ............... 424/85

FOREIGN PATENT DOCUMENTS

WO    WO 95/31202    * 11/1995    ......... A61K/31/555

OTHER PUBLICATIONS

Behm C A et al.: Novel Cationic Surfactants Derived from Metal Ion Cage Complexes: Potential Antiparasitic Agents, Australian Journal of Chemistry, vol. 48, No. 5, 1995, pp. 1009–1030, XP000573096.
Yeh et al.: Synthesis and Characterization of Cobalt–Cage Complexes with Pendant Phenol Groups Inorg. Chem., vol. 35, 1996, pp. 3828–3835, XP002191507.
Lawrence et al.: Organic Substituent Effects in Macrobicyclic (Hexaamine) cobalt (III/II) Complexes: A New Method of Obtaining Polar Substituent Constants, INORG. Chem., vol. 29, 1990, pp. 4808–4816, XP001056887.

SKOV: Effect of Protonation on the Electronic Spectra of Some Cobalt (III) Cage Complexes, ACTA Chem. SCAND., vol. 46, No. 5 1992, pp. 492–493, XP001056917.

Achilleos et al.: Synthesis and Characterization of Pendant Arm Encapsulated Complexes of Cobalt (III), Aust. J. Chem. vol. 42, No. 5, 1989, pp. 649–657, XP001056874.

Gerald A. Bottomley, et al., "The Synthesis and Structure of Encapsulating Ligands: Properties of Bicyclic Hexamines", Aust. J. Chem., 1994, vol. 47, pp. 143–179.

* cited by examiner

Primary Examiner—Michael G. Hartley
(74) Attorney, Agent, or Firm—Banner & Witcoff, Ltd.

(57) ABSTRACT

The present invention relates to cryptate compounds useful as chelating agents. In particular, the present invention relates to functionalized derivatives of certain cryptate compounds. These functionalized derivatives are suitable for use in radiolabelling and similar applications. The present invention also relates to a method for diagnosis or therapy of a disease utilizing functionalized derivatives of cryptase compounds. In one embodiment, the present invention relates to a compound which is capable of being radiolabelled of general formula (I) in which n represents an integer from 2 to 4, where each $R^4$ and $R^5$ is independently selected from —H, $CH_3$, COOH, $NO_2$, $CH_2OH$, $H_2PO_4$, $HSO_3$, CN, C=$ONH_2$ and CHO; X and Y are the same or different and are selected from the group of C—R, N, P and C—Z in which R represents a hydrogen or halogen atom or a hydroxyl, nitro, nitroso, amino, optionally substituted alkyl, optionally substituted aryl, optionally substituted aralkyl or cyano group, or a group of the formula —COOR', COCOOR', NH—$COCH_2Br$, —NH—CO—CH=CH—COOR' in which R' is a hydrogen atom or alkyl group; or, W is selected from the group of NH, S and O; and Z is a functionalized linkage group which is capable of binding said compound of formula (I) to a molecular recognition unit and wherein at least one of X and Y is C—Z; or a pharmaceutically acceptable salt thereof

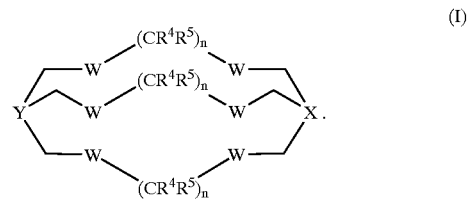

(I)

59 Claims, 8 Drawing Sheets

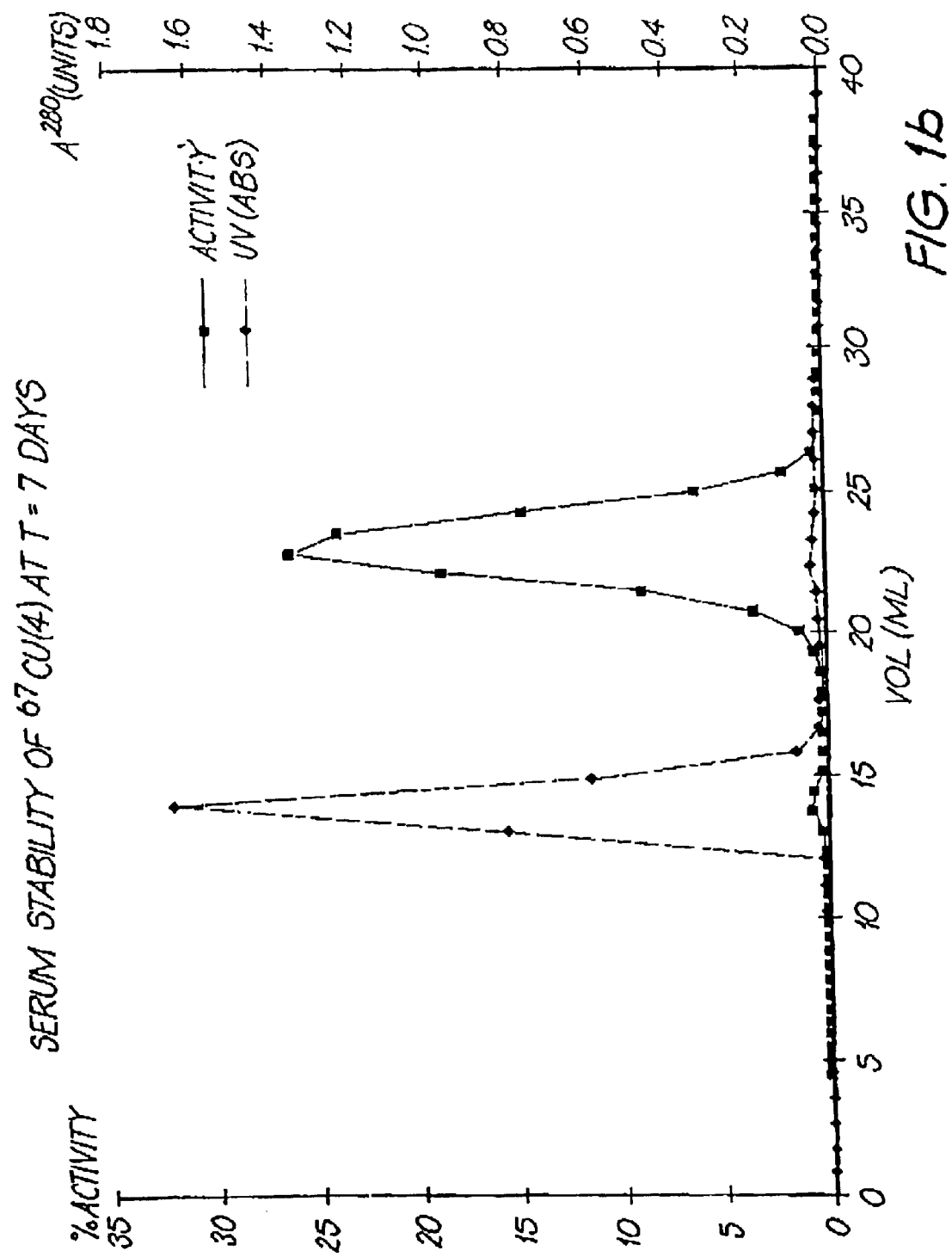

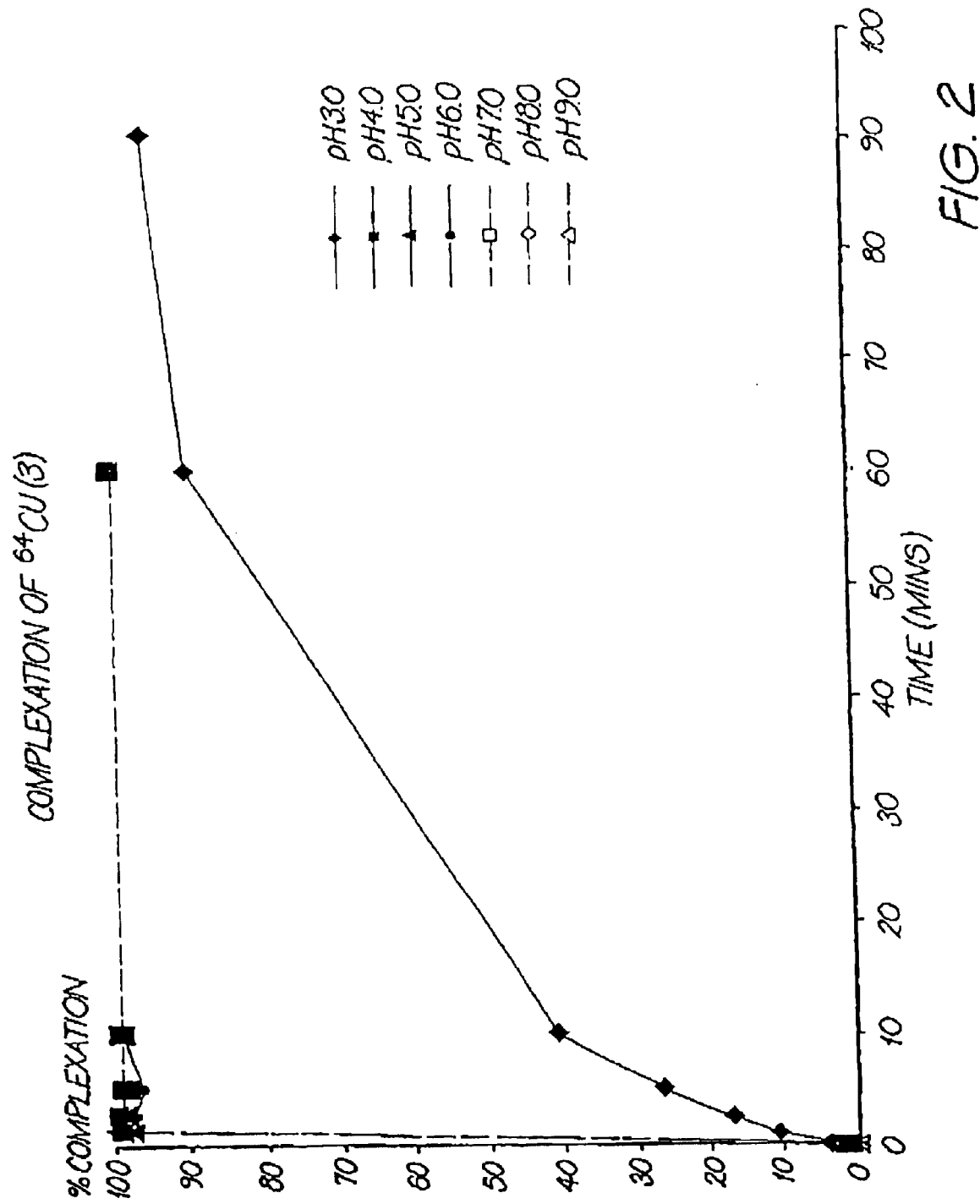

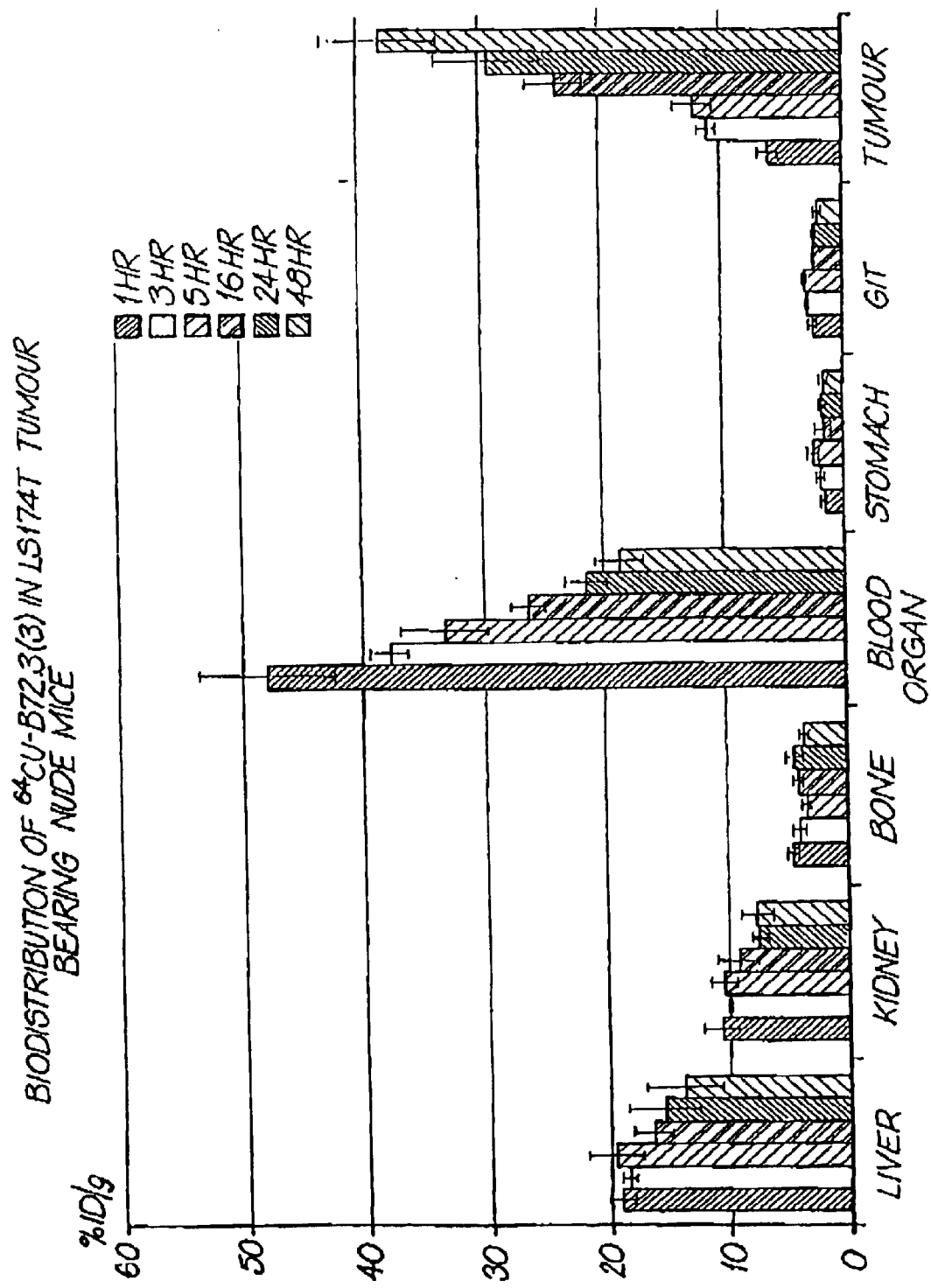

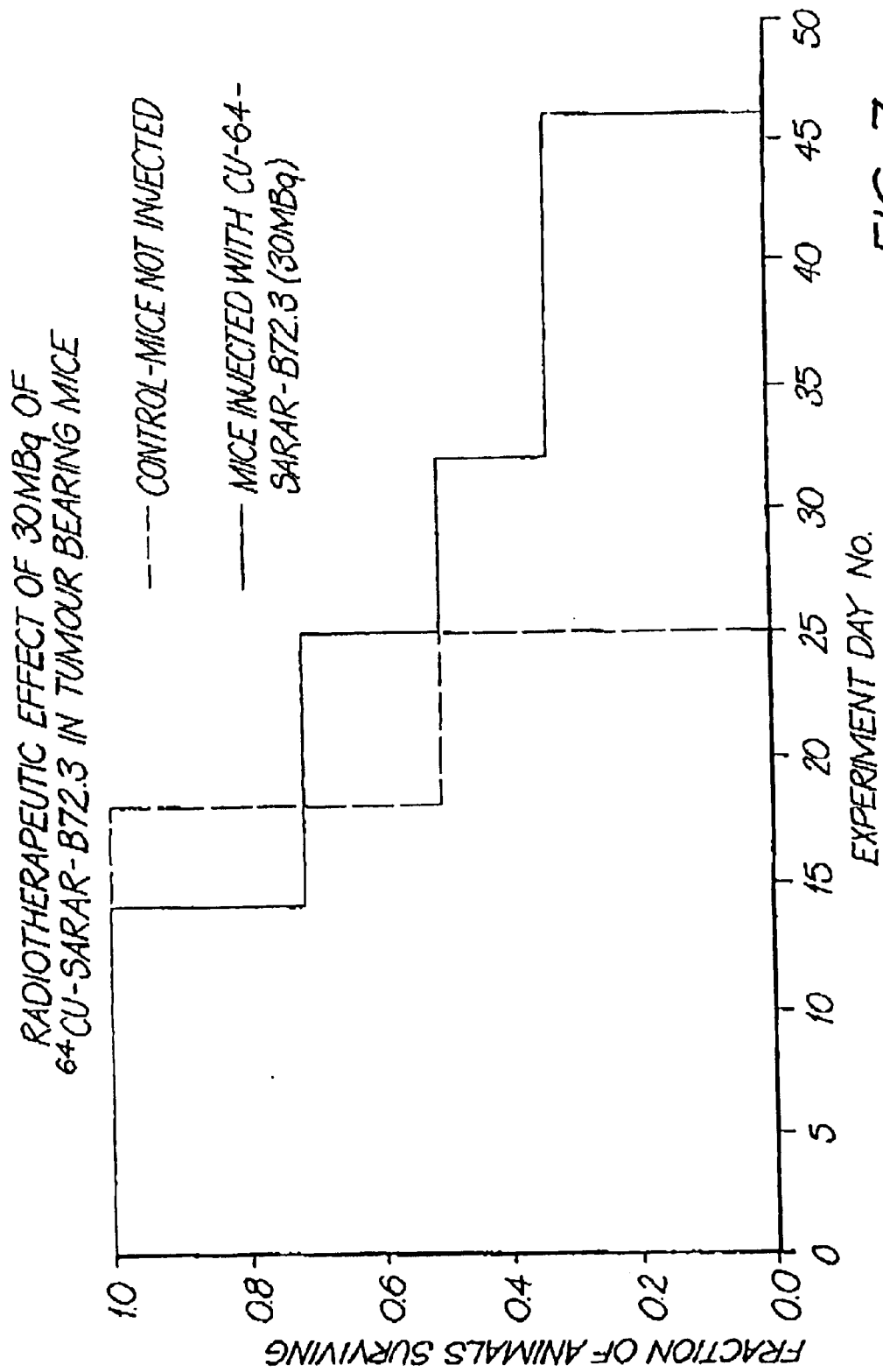

CRYPTATE COMPOUNDS AND METHODS FOR DIAGNOSIS AND THERAPY

TECHNICAL FIELD

The present invention relates to cryptate compounds useful as chelating agents. In particular, the present invention relates to functionalised derivatives of certain cryptate compounds. These functionalised derivatives are suitable for use in radiolabelling and similar applications. The present invention also relates to a method for diagnosis or therapy of a disease utilising functionalised derivatives of cryptate compounds.

BACKGROUND OF THE INVENTION

Radiolabelled compounds are useful as radiopharmaceuticals, imaging agents, or the like which are especially useful for but not limited to the diagnosis and therapy of diseases including cancer.

Known radiolabelled compounds suffer from the disadvantage that, in use, the radiolabelled nuclide can become detached from the carrier compound thereby leading to problems and potential complications in diagnostic and therapeutic applications. Further, the known radiopharmaceuticals tend to be non-specific in their biodistribution throughout a subject.

The present invention seeks to ameliorate the stated disadvantages of the prior art by providing compounds which are capable of being radiolabelled more expeditiously, specifically target a localised area of tissue or an organ in a subject and which are more stable than the prior art compounds and less toxic. Further, the compounds of the present invention are typically suitable for use in pharmaceutical formulations. It is a farther typical object of the present invention to provide a method of diagnosis or therapy of disease in a subject.

SUMMARY OF THE INVENTION

In accordance with a first embodiment of the present invention, there is provided a compound which is capable of being radiolabelled of general formula (I) which is as follows:

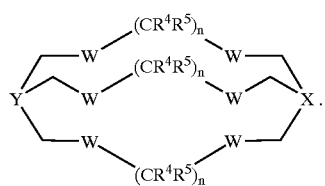

(I)

in which n represents an integer from 2 to 4,
where each $R^4$ and $R^5$ is independently selected from —H, $CH_3$, COOH, $NO_2$, $CH_2OH$, $H_2PO_4$, $HSO_3$, CN, C(=O)$NH_2$ and CHO;

X and Y are the same or different and are selected from the group of C—R, N, P and C—Z in which R is selected from hydrogen, halogen, hydroxyl, nitro, nitroso, amino, optionally substituted alkyl, optionally substituted aryl, optionally substituted aralkyl, cyano, —COOR', COCOOR', NH—COCH$_2$Br, —NH—CO—CH=CH—COOR' in which R' is a hydrogen atom or alkyl group;

W is selected from the group of NH, S and O; and

Z is a functionalised linkage group which is capable of binding said compound of formula (I) to a molecular recognition unit and wherein at least one of X and Y is C—Z; or a pharmaceutically acceptable salt thereof.

It is to be understood that throughout this specification, the term "molecular recognition unit" includes an antibody, protein, peptide, carbohydrate, nucleic acid, oligonucleotide, oligosaccharide, liposome, or other molecule which can form part of a specific binding pair.

In one form of the compound of Formula (I), the functionalised linkage group Z is selected from the group of halogen or other leaving group, nitro, nitroso, imide, dione of the formula,

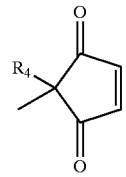

vinyl group of formula $Het^1$—C($Het^2$)=$CH_2$ (where $Het^1$ and $Het^2$ are the same or different and is each a nitrogen containing heterocyclic group or $Het^1$ is a nitrogen containing heterocyclic group and $Het^2$ is H), —C(=NH)O$R^2$, NCO, NCS, COR", COOR', $SR^2$, NHN$R^2R^3$, NHCONHN$R^2R^3$, NHCSNHN$R^2R^3$, CONR$^2R^3$, OR$^2$, NR$^2R^3$, $(CH_2)_pR^1$, $(CH_2)_pArR^1$, $(CH_2O)_pCH_2R^1$, $(CH_2OCH_2O)_qArR^1$, $(CHCH)_rR^1$, $(CHCH)_rArR^1$ where $R^2$ and $R^3$ are the same or different and are independently selected from H, $(CH_2)_pR^1$, $(CH_2)_pArR^1$, $(CH_2O)_pCH_2R^1$, —$(CH_2OCH_2O)_qArR^1$, $(CHCH)_rR^1$, $(CHCH)_rArR^1$ and where $R^1$ is selected from SH, OH, $NH_2$, COOH, NCS, —N=N, or —C(=NH)OCH$_3$, COR", where R" is H, halogen, $N_3$, alkoxy, OAr, imidyloxy, imidazoyloxy, alkyl, or alkyl substituted with a halogen or other leaving group, where p is an integer from 1 to 20, more typically 1 to 10, still more typically 1 to 4, even more typically 1 to 2 and yet more typically 1; q is an integer from 1 to 20, more typically 1 to 10, still more typically 1 to 4, even more typically 1 to 2 and yet more typically 1; r is an integer from 1 to 4, more typically 1 or 2, still more typically 1; and Ar is optionally substituted aryl or optionally substituted aralkyl, provided that when one of X and Y is selected from C—NO$_2$, C—OH, C—Cl, C—CH$_3$ or C—NH$_2$ then the other X or Y substituent cannot be selected from C—NO$_2$, C—OH, C—Cl or C—NH$_2$. In moieties of formula $(CH_2)_pR^1$, $(CH_2)_pArR^1$, one or more methylene groups may also be replaced with O, S, NH or carbonyl, for example C(O)$R^1$, $CH_2C(O)R^1$, NHCH$_2R^1$, NHC(O)$R^1$, $CH_2OR^1$, $CH_2C(O)NHR^1$, and the like.

Typically in the compound of Formula (I), the functionalised linkage group Z of the compound of Formula (I) is selected from the group of halogen, maleimide, a vinyl pyridyl group of formula

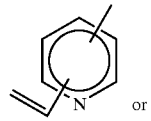 or

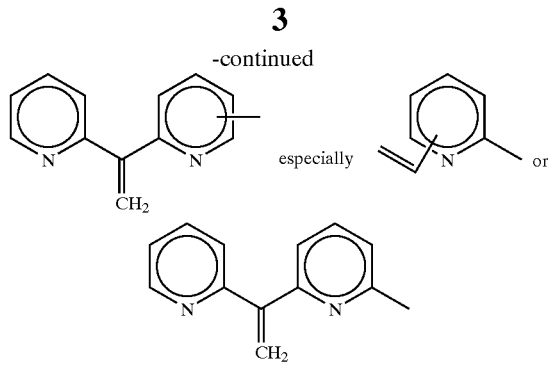

especially or or a dione of formula

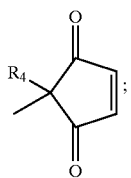

$NR^2R^3$ where $R^2$ and $R^3$ are the same or different and are independently selected from H, $(CH_2)_pR^1$, $(CH_2)_pArR^1$, $(CH_2O)_pCH_2R^1$, $—(CH_2OCH_2O)_qArR^1$, $—(CHCH)_rR^1$, $(CHCH)_rArR^1$ and where $R^1$ is selected from $NH_2$, COOH, NCS, NCO, $—N=N$, or $—C(=NH)OCH_3$, COR" group where R" is H, halogen, alkyl, or alkyl substituted with a halogen or other leaving group, where p is an integer from 1 to 20, more typically 1 to 10, still more typically 1 to 4, even more typically 1 to 2 and yet more typically 1; q is an integer from 1 to 20, more typically 1 to 10, still more typically 1 to 4, even more typically 1 to 2 and yet more typically 1; r is an integer from 1 to 4, more typically 1 or 2, still more typically 1; and Ar is optionally substituted aryl or optionally substituted aralkyl, provided that at least one of $R^2$ and $R^3$ is other than hydrogen, and wherein, in moieties of formula $(CH_2)_pR^1$, $(CH_2)_pArR^1$, one or more methylene groups may also be replaced with O, S, NH or carbonyl, for example $C(O)R_1$, $CH_2C(O)R^1$, $NHCH_2R^1$, $NHC(O)R^1$, $OR^1$, $SR^1$, $CH_2OR^1$, $CH_2C(O)NHR^1$, and the like.

More typically in a compound of Formula (I), each $R^4$ and $R^5$ is H; W is NH; n is 2 to 4, more typically 2 or 3, still more typically 2; Z is selected from halogen and $NR^2R^3$ where $R^2$ and $R^3$ are the same or different and are independently selected from H, $(CH_2)_pR^1$, $(CH_2)_pArR^1$, provided that at least one of $R^2$ and $R^3$ is other than H; $R^1$ is selected from $NH_2$, COOH, NCS, $NHCOCH_2Br$ and COR" where R" is halogen, typically Br; and p is an integer from 1 to 4, more typically 1 to 2 and still more typically 1. Yet more typically, $R^1$ is $NH_2$. Typically, R is amino, nitro, hydroxy or halogen and still more typically R is amino.

As used herein, the term "aryl" refers to single, polynuclear, conjugated and fused residues of aromatic hydrocarbons or aromatic heterocyclic ring systems. Examples of such groups are phenyl, biphenyl, terphenyl, quaterphenyl, naphthyl, tetrahydronaphthyl, anthracenyl, dihydroanthracenyl, benzanthracenyl, dibenzanthracenyl, phenanthracenyl, fluorenyl, pyrenyl, indenyl, azulenyl, chrysenyl, pyridyl, 4-phenylpyridyl, 3-phenylpyridyl, thienyl, furyl, pyrryl, indolyl, pyridazinyl, pyrazolyl, pyrazinyl, thiazolyl, pyrimidinyl, quinolyl, isoquinolyl, benzofuranyl, benzothienyl, purinyl, quinazolinyl, phenazinyl, acridinyl, benzoxazolyl, benzothiazolyl, heteroaryl, pyridine and Het—$CH=CH_2$ and the like. Typically aryl is phenyl, pyridyl, naphthyl, anthracenyl or the like, and heteroaryl is typically pyridine and Het—$CH=CH_2$. Still more typically, aryl is phenyl.

As used herein, the term "aralkyl" refers to alkyl groups substituted with one or more aryl groups as previously defined. Examples of such groups are benzyl, 2-phenylethyl and 1-phenylethyl.

As used herein, the term "optionally substituted" means that the moiety described as optionally substituted may carry one or more substituents selected from amino, halogen, hydroxy, mercapto, nitro, cyano, thiocyano, alkyl, alkoxy, halogenoalkyl, acyl, acylamino, acyloxy, carboxyl, alkoxycarboxyl, carbamoyl, pyridoylamino, carboxyalkylcarbamoyl, N-carboxyalkylcarbamoyl, sulpho, sulphamoyl, mono- or dialkylated or phenylated sulphamoyl which can carry one or more alkyl substituents, alkylsulphonyl, alkoxysulphonyl, optionally hydroxy-containing phenylsulphonyl or phenoxy sulphonyl.

In another form of the compound of Formula (I), the Z group of said compound of Formula (I) is selected from the group of $NR^2R^3$ where $R^2$ and $R^3$ together with the nitrogen atom to which they are attached form a substituted saturated or unsaturated 3 to 8 membered ring optionally containing one or more additional heteroatoms O, S or N and wherein there is at least one substituent capable of binding said compound of Formula (I) with a molecular recognition unit.

In accordance with a second embodiment of the present invention, there is also provided a compound of Formula (I) as described in the first embodiment of the present invention which is complexed with a metal ion.

The metal ion is typically selected from $^{64}Cu$, $^{67}Cu$, $^{99m}Tc$, Ga, In, Co, Re, Fe, Au, Ag, Rh, Pt, Bi, Cr, W, Mo, Ni, V, Pb, Ir, Pt, Zn, Cd, Mn, Ru, Pd, Hg, Ti, Tl, Sn, Zr, and the lanthanide group of elements in the Periodic Table such as Sm, Ho, Gd, Tb, Sc, Y, and the actinides.

The metal ion is further typically a radionuclide selected from the group of $^{64}Cu$ $^{67}Cu$, $^{99m}Tc$, and radionuclides of In(III), Ga (III), Fe (III), Cu (II), Ti (IV) and other radionuclides from the Lanthanides, Re, Sm, Ho, and Y.

In accordance with a third embodiment of the present invention, there is also provided a pharmaceutical formulation comprising a compound of Formula (I) as described the first embodiment of the present invention or a metal complex, radiolabelled complex or pharmaceutically acceptable salt thereof together with a pharmaceutically acceptable carrier.

In accordance with a fourth embodiment of the present invention, there is also provided a diagnostic formulation comprising a compound of Formula (I) as described in the first embodiment of the present invention or a metal complex, radiolabelled complex or pharmaceutically acceptable salt thereof and a reducing agent in a pharmaceutically acceptable carrier.

In accordance with a fifth embodiment of the present invention, there is also provided a method of diagnosis or therapy in a subject comprising administering to the subject a diagnostically or therapeutically effective amount of a compound of Formula (I) as described in the first embodiment of the present invention or a metal complex, radiolabelled complex or a pharmaceutically acceptable salt thereof.

In accordance with a sixth embodiment of the present invention, there is also provided a use of a compound of Formula (I) or a metal complex, radiolabelled complex or pharmaceutically acceptable salt thereof in the preparation of a medicament for diagnosis or therapy of disease in a subject.

In accordance with a seventh embodiment of the present invention, there is also provided a compound of Formula (I)

as described in the first embodiment of the present invention or a metal complex, radiolabelled complex or pharmaceutically acceptable salt thereof when used in the diagnosis or therapy of disease in a subject.

In accordance with an eighth embodiment of the present invention, there is also provided a conjugate compound comprising at least one compound of Formula (I) as described in the first embodiment of the present invention or a metal complex, radiolabelled complex or a pharmaceutically acceptable salt thereof bonded to at least one molecular recognition unit comprising an antibody, protein, peptide, carbohydrate, oligonucleotide, oligosaccharide, liposome or the like.

In accordance with a ninth embodiment of the present invention, there is provided a method of diagnosis or therapy in a subject comprising administering to the subject a diagnostically or therapeutically effective amount of a conjugate compound as described in the eighth embodiment of the present invention.

In accordance with a tenth embodiment of the present invention, there is provided a use of a conjugate compound as described in the eighth embodiment of the present invention in the preparation of a medicament for diagnosis or therapy of disease in a subject.

In accordance with an eleventh embodiment of the present invention, there is provided a conjugate compound as described in the eighth embodiment of the present invention when used in the diagnosis or therapy of disease in a subject.

In accordance with a twelfth embodiment of the present invention, there is provided ax method of imaging a subject comprising introducing a compound of Formula (I) or a metal complex, radiolabelled complex, conjugate compound or pharmaceutically acceptable salt thereof to a subject.

In accordance with a thirteenth embodiment of the present invention, there is provided a use of a compound of Formula (I) or a metal complex, radiolabelled complex, conjugate compound or pharmaceutically acceptable salt thereof in the preparation of a medicament for imaging in a subject.

In accordance with a fourteenth embodiment of the present invention, there is provided a compound of Formula (I) or a metal complex, radiolabelled complex, conjugate compound or pharmaceutically acceptable salt thereof when used in imaging in a subject.

In accordance with a fifteenth embodiment of the present invention, there is provided a compound of Formula (I) having the following structure:

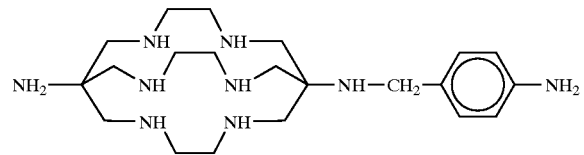

DETAILED DESCRIPTION OF THE INVENTION

The compounds of Formula (I) typically comprise those compounds where n represents an integer from 2 to 4, more typically 2 or 3, still more typically 2. Typically, one of X and Y is a C—Z group where Z is typically $NR^2R^3$ where $R^2$ and $R^3$ are the same or different and are selected from H, $(CH_2)_pR^1$ and $(CH_2)_pArR^1$, where $R^1$ is as previously defined, and p is 1 to 4, more typically 1 to 2 and still more typically 1, provided that at least one of $R^2$ and $R^3$ is other than hydrogen. Usually, one of X is a C—Z group and the other is a group C—R, where R is as previously defined, typically amino, lower alkyl, nitro, hydroxy or halogen. Generally, $R^1$ is $NH_2$ and p is 1.

An example of a compound of Formula (I) is:

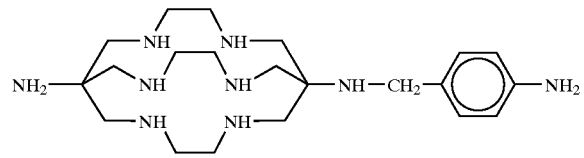

The $R^1$ group in a compound of Formula (I) may provide a point of attachment of a compound of Formula (I) to a molecular recognition unit.

The molecular recognition unit is typically an antibody, protein, peptide, oligonucleotide, oligosaccharide. In particular, the molecular recognition unit is typically an antibody and more typically a monoclonal antibody.

Thus, compounds of Formula (I) provide a method of attachment of radionuclide metal ions such as In(III), Ga(III), Fe(III), Tc(IV) or Tc(V), Re(VII), Cu(II), Ti(IV), other radionuclides from the Lanthanides, Rhenium, Samarium, Holmium, Yttrium and the like to molecular recognition units such as monoclonal antibodies, receptor specific proteins, peptides or oligonucleotides for in vivo imaging and therapy.

The compounds of general Formula (I) are typically prepared by attachment of a functional linking group to a suitable cryptate. Methods of synthesis of cryptates useful as precursors to compounds of Formula (I) in which W is NE are described in U.S. Pat. No. 4,497,737 in the name of Sargeson et al, the disclosure of which is incorporated herein by reference. Other cryptates where W is S or O may be prepared by analogous methods. Sargeson et al describe synthesis of metal cage "cryptate" compounds by the condensation of a tris-(diamine) metal ion complex as described at column 3 lines 30 to 35 with formaldehyde and an appropriate nucleophile. In order to obtain the compounds of Formula (I), an appropriate nucleophile is selected so as to obtain the desired functionalised linkage group Z as defined in Formula (I). In particular, reference is made to column 4 lines 17 to 27 of U.S. Pat. No. 4,497,737. Alternatively, a functionalised linkage group Z may be attached to a functional group of a cryptate prepared by the methods taught by Sargeson et al (for example see Example 9 at column 9 line 65 to column 12 line 10 of Sargeson et al) by standard synthetic techniques. If necessary, a protecting group may be introduced into the cryptate structure to protect latent functionality for the desired functionalised linkage group Z as defined in Formula (I) during synthesis of the desired cryptate precursor. Suitable protecting groups are described, for example in Greene, T. W., *Protective Groups in Organic Synthesis* (John Wiley & Sons, New York, 1981) and McOmie, J. F. W., *Protective Groups in Organic Chemistry* (Plenum Press, London, 1973).

For example, compounds of Formula (I) where said Z group comprises a mono- or di-substituted amino group and where the substituent is optionally substituted alkyl, are readily prepared by treating the amino compound with the appropriate halo-substituted alkyl. Typically, the compound of Formula (I) where Z is —NH—$CH_2$—$CH_2$—$NH_2$ can be prepared by treating a compound of Formula (I) where R is $NH_2$ with $BrCH_2CH_2NH_2$ in the presence of $NaHCO_3$ or the like with suitable protection.

Compounds of formula (I) where $R^1$ is —NCS may be prepared by reacting the amino compound with thiophosgene (see WO87/12631), Kozak et al., Cancer Res. 49, 2639 (1989). Substituted acid halide compounds are produced by reacting a compound of formula (I) where R is $NH_2$ with $BrCH_2COBr$ at 4° C. according to the procedure of C J Mathias et al., Bioconjugate Chem., 1, 204 (1990). Compounds with an electrophilic moiety can also be prepared by methods known in the art, such as in ACC Chem. Res. 17 202–209 (1984). Compounds with active esters $(CH)_p$—C(O)—X may be formed by the procedures of Bodanszky M, *The Peptide. Analysis Synthesis Biology*, Ed. E. Gross and J Meienhofer, Vol 1, pp 105–196, Academic Press, Inc., Orlando, Fla. (1979) and Bodanszky M, *Principles of Peptide Synthesis*, pp 9–58, Springerverlag, N.Y., (1984). Other compounds of formula (I) may be prepared from such compounds by standard procedures such as described in Modern Synthetic Reactions, H O House, $2^{nd}$ Edition, Benjamin, Inc. Philippines, 1972.

In a typical embodiment, compounds of formula (I) in which X or Y is C—Z where the group Z is a group $NH(CH_2)_pR^1$ or $NH(CH_2)_pArR^1$ may be prepared by a Schiff Base condensation reaction of a compound of formula (I) (or a metal complex thereof) in which X or Y is $NH_2$ with an aldehyde of formula $HC(O)(CH_2)_{p-1}R^1$ or $HC(O)(CH_2)_{p-1}ArR^1$. (Still typically, the Schiff Base condensation reaction is most appropriately conducted between a copper complex of compounds of Formula (I) in which X or Y is $NH_2$ with an aldehyde of formula $HC(O)(CH_2)_{p-1}R^1$ or $HC(O)(CH_2)_{p-1}R^1$.) In one particular form of this embodiment, a compound of formula (I) is obtained by the reaction of nitrobenzaldehyde with the copper complex of an aminocryptate such as described by Sargeson et al. The reaction is typically performed in an inert-gas atmosphere and in the presence of solvent and diluents typically inert to the reactants. Suitable solvents comprise aliphatic, aromatic, or halogenated hydrocarbons such as benzene, toluene, xylenes; chlorobenzene, chloroform, methylene chloride, ethylene chloride; ethers and ethereal compounds such as dialkyl ether, ethylene glycol mono or -dialkyl ether, THF, dioxane; alkanols such as methanol, ethanol, n-propanol, isopropanol; ketones such as acetone, methyl ethyl ketone; nitriles such as acetonitrile or 2-methoxypropionitrile; N,N-dialkylated amides such as dimethylformamide; dimethylsulphoxide, tetramethylurea; as well as mixtures of these solvents with each other. If the amine or a salt thereof is soluble in water, then the reaction medium may be water at low temperature. The compounds of formula (I) may be converted to pharmaceutically acceptable salts by way of recognised procedures.

Typically, for medical use salts of the compounds of the present invention will be pharmaceutically acceptable salts; although other salts may be used in the preparation of the inventive compound or of the pharmaceutically acceptable salt thereof. By pharmaceutically acceptable salt is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art.

Suitable pharmaceutically acceptable salts of the compounds of the present invention may be prepared by mixing a pharmaceutically acceptable acid such as hydrochloric acid, sulphuric acid, methanesulphonic acid, succinic acid, fumaric acid, maleic acid, benzoic acid, phosphoric acid, acetic acid, oxalic acid, carbonic acid, tartaric acid, or citric acid Suitable pharmaceutically acceptable salts of the compounds of the present invention therefore include acid addition salts.

For example, S. M. Berge el al. describe pharmaceutically acceptable salts in detail in *J. Pharmaceutical Sciences*, 1977, 66:1–19. The salts can be prepared in situ during the final isolation and purification of the compounds of the invention, or separately by reacting the tree base function with a suitable organic acid. Representative acid addition salts include acetate, adipate, alginate, ascorbate, asparate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The radiolabelling of compounds of formula (I), and salts thereof can be accomplished by using procedures recognised in the art. For example, radiolabelling of the chelator with $^{67}Cu$ can be achieved by adding copper in an aqueous acetate solution to a compound of formula (I) in an aqueous solution and incubating at room temperature.

Alternatively, the radiolabelling of a compound of formula (I) with technetium, for example, may be achieved by adding a reducing agent such as stannous salts typically stannous chloride, to an aqueous solution of a compound of formula (I), followed by reaction with aqueous sodium pertechnetate solution ($Na^{99m}TcO_4$). The order of mixing rd these three components is believed not to be critical. However, typically the reducing agent is added to the chelator of formula (I). Other suitable reducing agents comprise alkali metal dithionites such as sodium dithionite, sodium borohydride, hydrochloric acid, hydrobromic acid, other soluble dithionites such as potassium dithionite or ammonium dithionite, a soluble bisulfite or metabisulfite such as sodium bisulfite, potassium bisulfite, lithium bisulfite, ammonium bisulfite, sodium metabisulfite, potassium metabisulfite, lithium metabisulfite or ammonium metabisulfite, or an aqueous solution of sulfur dioxide.

Technetium-99m in the form of an aqueous solution of sodium pertechnetate is readily obtainable from commercially available molybdenum-99/technetium-99m generators or alternatively, instant $^{99m}Tc$ may be used. Cu-64 is commercially available from Australian Nuclear Science & Technology Organisation and $^{67}Cu$ from the US Department of Energy, Brookhaven, USA.

The conjugate compounds of the eighth embodiment of this invention may be formed by the reaction of a radiolabelled metal complex of a compound of Formula (I) together with a molecular recognition unit. The radionuclides which are useful for complexing with the compounds of Formula (I) typically comprise metal ions which have at least two oxidation states, most typically an oxidation state of +2 or +3. In a typical embodiment, the radiolabelled metal complex is selected from $^{64}Cu$, $^{67}Cu$ and $^{99m}Tc$, Sm, Ho, Re, Sc, Cu, Pd, Rh, and Y. The most typical metal ions comprise $^{64}$Cu, $^{67}$Cu, $^{99m}$Tc. These radiolabelled metal complexes are then reacted with a molecular recognition unit. The radiolabelled molecular recognition unit so formed is useful for diagnostic, therapeutic and radioimaging applications.

Alternatively a conjugate of a compound of formula (I) may be first prepared, and then it may be radiolabelled.

Thus, radiolabelling of molecular, recognition units such as proteinaceous materials using compounds of formula (I) can be conducted in two ways, namely:
(a) prelabelling of a compound of Formula (I) with a suitable radionuclide, followed by conjugation of the resultant radiocomplexed compound to proteinaceous or other material, or
(b) conjugating the compound of formula (I) to proteinaceous or other material for subsequent radiolabelling.

The formation of a conjugate compound of formula (I) is usually achieved by the reaction of the functionalised linkage group with a thiol, amino, carboxyl, hydroxyl, aldehyde, aromatic or heteroaromatic group present in the molecular recognition unit. For example, an amino or hydroxy group of the functionalised linkage group may be reacted with a free carboxyl group of the molecular recognition unit, or vice versa. Suitably a coupling agent such as a carbodiimide may be employed to facilitate the coupling reaction.

The conjugate compounds according to the eighth embodiment of the present invention may contain more than one molecule of a compound of formula (I) to any one molecular recognition unit. The metal complexing and radiolabelling of compounds of formula (I), and pharmaceutically acceptable salts thereof can be accomplished by using procedures recognised in the art. For example, the radiolabelling of the conjugate compounds with $^{64}$Cu may be achieved by adding an aqueous acetate solution of $^{64}$Cu to the conjugate compound in an aqueous solution and incubating for 5 minutes at room temperature. A composition comprising an uncomplexed conjugate in accordance with the invention may also be supplied to radio-chemists, technicians, radiopharmacists, doctors or the like in the form of a kit for radiolabelling immediately prior to use.

In a typical form of this invention, the kit comprises a first container that contains a radiolabelling metal ion, usually in solution, and a second container that contains a conjugate compound as described in the eighth embodiment of the present invention. The kit, in use, then involves mixing the contents of said first and second containers to obtain the radiolabelled conjugate compound.

Typically, the compounds of Formula (I) or the metal complex, radiolabelled complex or pharmaceutically acceptable salt thereof are useful for labelling molecular recognition units for use in methods of diagnosis and therapy of disease. In particular, the typical radiolabelled molecular recognition units are monoclonal antibodies and fragments thereof, peptides, oligonucleotides, oligosaccharides or liposome or a part of a specific binding pair.

The applications of radiolabelled molecular recognition units comprise diagnosis, imaging and therapy of disease such as cancer. Typically, the compounds of formula (I) and their metal complexes and/or salts thereof have a diagnostic use as imaging agents in vitro and in vivo. The method of diagnosis using the aforesaid imaging agents will result from the localisation of the radiolabelled conjugate compounds on specific organs and tissues in a subject.

The method of diagnosis will typically involve first the administration of an effective amount of a radiolabelled compound of Formula (I) to a subject; and then monitoring the subject after a suitable period of time in order to ascertain the presence or absence of a cancer for example as evidenced by localisation of the radiolabel at a particular site in the subject. Typically, the monitoring step shall provide information regarding the location of any cancer if it is present. The effective amount or dosage of the radiolabelled compound of Formula (I) will depend upon the desired amount of radioactivity required for the diagnostic application balanced with the safety requirement of not exposing the subject, in particular their organs and tissues, to harmful amounts of radiation. Appropriate dosages for any given application may be determined by persons skilled in the relevant art by no more than routine experimentation, given the teaching herein.

The method of therapy will typically involve compounds of formula (I) or the metal complexes, radiolabelled complexes and/or pharmaceutically acceptable salts thereof which are useful as cytotoxic agents. In a typical embodiment, the therapy of disease comprises treatment of cancer, abnormal cell disorders and the treatment of tumours. In such applications, the radiolabelled compound of formula (I) is typically conjugated to a molecular recognition unit which is capable of binding specifically to the tumour or abnormal cell. Examples of such molecular recognition units comprise one part of specific binding pairs and are known to persons skilled in the relevant art and typically comprise antibody/antigen pairs and the like.

The method of therapy will typically involve the administration of an effective amount of a radiolabelled compound of Formula (I) to a subject. The effective amount or dosage will depend upon the desired amount of radioactivity required for the diagnostic application balanced with the safety requirement of not exposing the subject, in particular their organs and tissues, to harmful amounts of radiation. Appropriate dosages for any given application may be determined by persons skilled in the relevant art by no more than routine experimentation, given the teaching herein.

Typically the treatment would be for the duration of the condition, and contact times would typically be for the duration of the condition.

Further, it will be apparent to one of ordinary skill in the art that the optimal quantity and spacing of individual dosages of a compound of the present invention will be determined by the nature and extent of the condition being treated, the form, route and site of administration, and the nature of the particular vertebrate being treated. Also, such optimum conditions can be determined by conventional techniques.

It will also be apparent to one of ordinary skill in the art that the optimal course of treatment, such as, the number of doses of the compound of the present invention given per day for a defined number of days, can be ascertained by those skilled in the art using conventional course of treatment determination tests.

Also included within the scope of the present invention are prodrugs of the inventive compound. Typically, prodrugs will be functional derivatives of a compound of Formula (I) in accordance with the first embodiment of the invention, which are readily converted in vivo to the required compound for use in the present invention as described herein. Typical procedures for the selection and preparation of prodrugs are known to those of skill in the art and are described, for instance, in H. Bundgaard (Ed), *Design of Prodrugs*, Elsevier, 1985.

When used in the treatment of disease, the compound of Formula (I) in accordance with the first embodiment of the invention or a metal complex, radiolabelled complex or a pharmaceutically acceptable salt thereof, may be administered alone. However, it is generally preferable that these compounds be administered in conjunction with other chemotherapeutic treatments conventionally administered to patients for treating disease. For example, a tumour may be treated conventionally with surgery, and the compound of Formula (I) in accordance with the first embodiment of the invention or a metal complex, radiolabelled complex or a pharmaceutically acceptable salt thereof, to extend the dormancy of micrometastases and to stabilise and inhibit the growth of any residual primary tumour.

Typically, when used in the treatment of solid tumours, compounds of the present invention may be administered with chemotherapeutic agents such as: adriamycin, taxol, fluorouricil, melphalan, cisplatin, alpha interferon, COMP (cyclophosphamide, vincristine, methotrexate and prednisone), etoposide, mBACOD (methortrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triazines including dacarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

When used in the treatment of disease, the compound of Formula (I) in accordance with the first embodiment of the invention or a metal complex, radiolabelled complex or a pharmaceutically acceptable salt thereof, may be administered alone. However, it is generally preferable that they be administered as pharmaceutical formulations. In general pharmaceutical formulations of the present invention may be prepared according to methods which are known to those of ordinary skill in the art and accordingly may include a pharmaceutically acceptable carrier, diluent and/or adjuvant.

These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g. intravenous, intraspinal, subcutaneous or intramuscular) route. In addition, the compound of Formula (I) in accordance with the first embodiment of the invention or a metal complex, radiolabelled complex or a pharmaceutically acceptable salt thereof, may be incorporated into biodegradable polymers allowing for sustained release, the polymers being implanted in the vicinity of where drug delivery is desired, for example, at the site of for example, a tumour or implanted so that the active agents are slowly released systemically. Osmotic minipumps may also be used to provide controlled delivery of high concentrations of the active agents through cannulae to the site of interest such as directly into for example, a metastatic growth or into the vascular supply to that tumour.

The carriers, diluents and adjuvants must be "acceptable" in terms of being compatible with the other ingredients of the formulation, and not deleterious to the recipient thereof.

Examples of pharmaceutically and veterinarily acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

For administration as an injectable solution or suspension, non-toxic parenterally acceptable diluents or carriers can include, Ringer's solution, isotonic saline, phosphate buffered saline, ethanol and 1,2 propylene glycol.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The radiolabelled molecular recognition units especially radiolabelled antibodies are particularly useful in medicine, for example, in locating specific tissue types and in the therapy of cell disorders. The radiolabelled antibodies can also be used to target metal ions to a specific tissue type, both in vitro and in vivo.

A typical use of the radiolabelled compounds of Formula (I): is to radiolabel monoclonal antibodies specific for colon, ovarian, lymphoma, breast and/or bladder cancer, with beta emitter radionuclides of metals such as Sm, Ho, Re, Sc, Cu, Pd, Pb, Rh and Y for therapy of above mentioned cancer. A further typical use is in the radiolabelling of a monoclonal antibody specific for metastasis of colon cancer for diagnosis and therapy.

In another typical embodiment, the antibody in the conjugate compound may be a complete antibody molecule or a fragment thereof or an analogue of either of these, provided that the antibody comprises a specific binding region. The antibody may be a humanised monoclonal or a fragment thereof. The antibody may also be a recombinant antibody. The antibody may be specific for any number of antigenic determinants, but is typically specific for one antigenic determinant.

In another typical embodiment, there is provided radiolabelling of monoclonal antibodies with $^{67}$Cu (beta and gamma emitter) and $^{64}$Cu (positron and beta emitter), for combined radioimmunoscintography (RIS) (SPECT and PET) and radioimmunotherapy (RIT). Other radionuclides comprise Auger emitting agents where the compound of Formula (I) is coupled to the monoclonal antibody and labelled with auger emitting isotope such as Fe-59 or Cu-64.

In still another typical embodiment, there is provided a two step pretargeted radioimmunotherapy where a monoclonal antibody with a first marker molecule attached thereto is injected into a subject. Once the antibody has cleared from the system and localised to the tumour, a second injection is administered to the subject. This second injection typically involves the radiolabelled complex of Formula (I) attached to a second marker molecule which recognises the first marker molecule on the targeted antibody. Alternatively, the second injection may typically be the second marker molecule alone and when cleared from the system, the radiolabelled complex of Formula (I) attached to the first marker molecule is administered to the subject. Both procedures provide amplification of the target site and reduce exposure of the radiolabelled complex to normal tissue. Still typically, the first marker molecule is biotin and the second marker molecule is avidin or streptavidin. Still more typically, the first marker molecule is smaller than the targeted antibody.

The invention also provides a two step procedure which involves the administration of an antibody-DNA conjugate or antibody-oligonucleotide conjugate followed by targeting with a radiolabelled complementary DNA or complementary oligonucleotide. This procedure also provides amplification of the target site and reduces exposure complex of the radiolabelled to normal tissue.

The invention also provides a use of compounds of Formula (I) or metal complexes, radiolabelled complexes, conjugate compounds or pharmaceutically acceptable salts thereof as Magnetic Resonance Imaging (MRI) agents. In this form of the invention, there is typically formed a complex of compound of formula (I) or a conjugate of the eighth embodiment, with a paramagnetic metal ion, typically Fe (III), Mn(II), which may be used as a contrast agent to enhance images. Further, complexes such as these may be employed in the form of a pharmaceutical formulation where the complex is present with a pharmaceutically acceptable carrier, excipient or vehicle therefor.

The pharmaceutical formulations described for the different embodiments of this invention typically comprise a formulation in the form of a suspension, solution or other suitable formulation. Physiologically acceptable suspending media together with or without adjuvants may be used. Still typically, the pharmaceutical formulations are in a liquid form and still more typically are in an injectable form. Still more typically, the injectable formulations are dissolved in suitable physiologically acceptable carriers which are recognised in the art.

The industrial use of the compounds of formula (I) further comprises their attachment to solid surfaces such as polymers, for use in the concentration of metal ions and purification of water or attached to an electrode surface for detection of specific metal ions.

BRIEF DESCRIPTION OF THE DRAWINGS

The present invention will be further illustrated, by way of example only, with reference to the accompanying figures; in which:

FIGS. 1a and 1b are graphical representations of the serum stability of $^{67}$Cu complex of compound (4) at 0 and 7 days respectively;

FIG. 2 is a graphical representation of the effect of pH on the complexation of $^{64}$Cu with compound (3);

FIG. 6 is a graphical representation of the biodistribution of $^{64}$Cu labelled conjugate of B72.3 conjugated with compound (3) in Tumour Bearing Nude Mice.

FIG. 7 is a graphical representation of the radiotherapeutic effect of 30MBq of $^{64}$Cu labelled conjugate of B72.3 conjugated with compound (3) in Tumour Bearing Nude Mice.

EXAMPLES

Figure 1A:
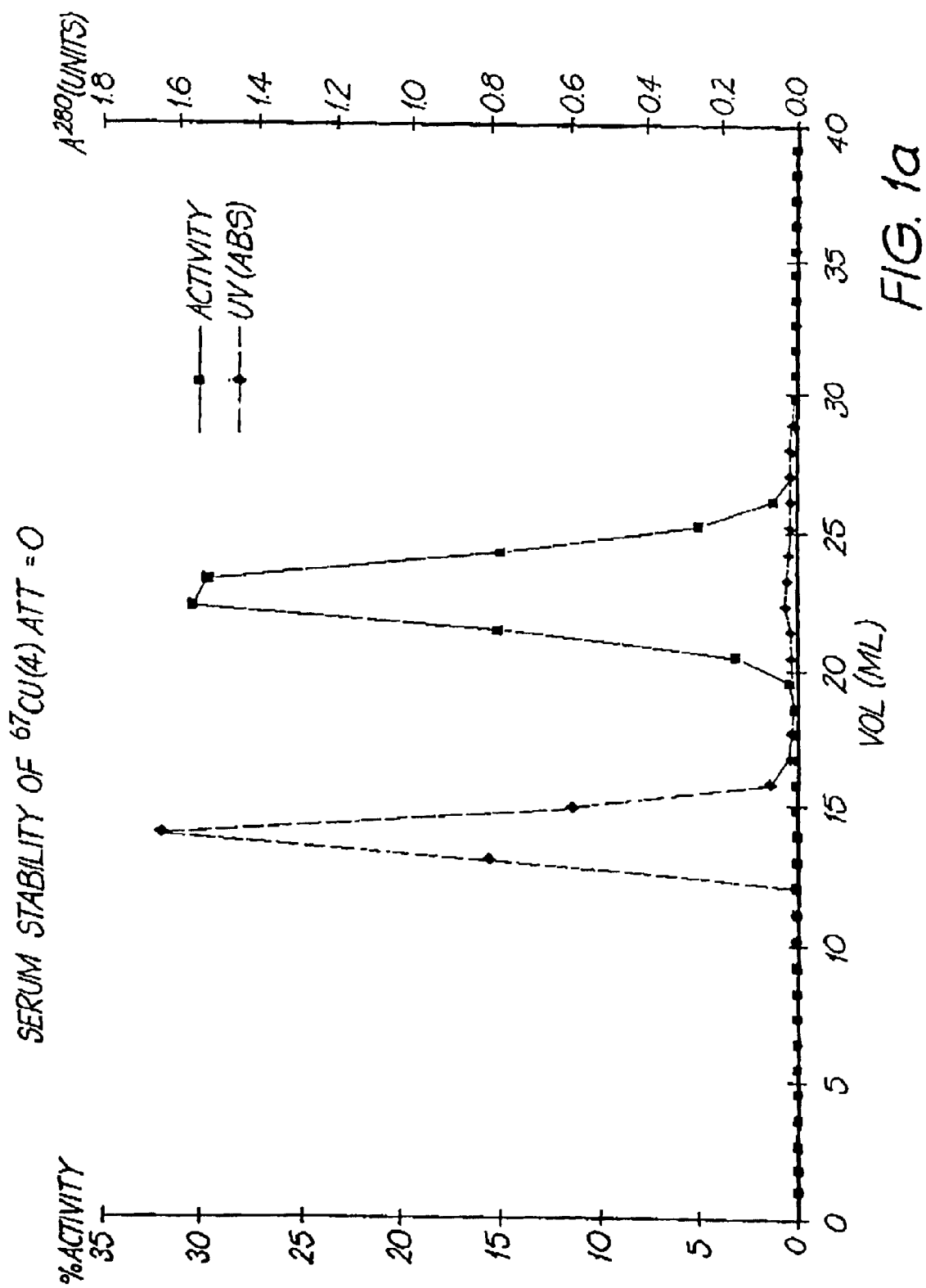

The following examples serve only to illustrate the invention and should not be construed as limiting the generality of the above description.

Example 1

Preparation of Compound (3)

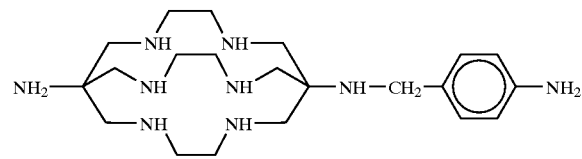

Compound (3)

Preparation of compound (3) is illustrated in Schemes 1 and 2.

Scheme 1
Schiff Base Condensation reaction of compound (1) with p-nitrobenzaldeheyde

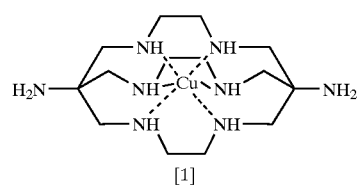

[1]

NO$_2$—⌬—CHO in EtOH + NaBH$_3$CN + CH$_3$COOH

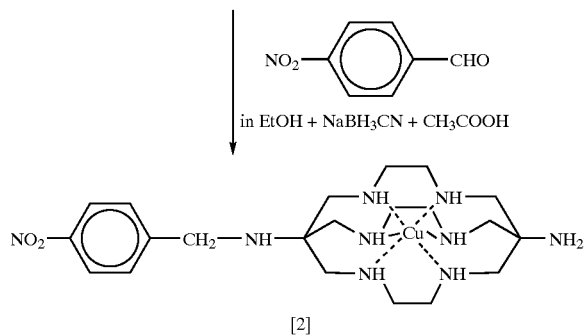

[2]

Scheme 2
Reduction of compound (2) to compound (3)

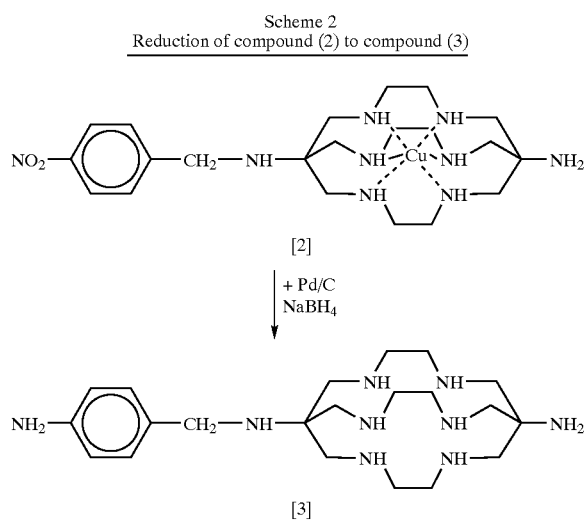

A. Preparation of Compound (2)

Compound (2) is prepared by Schiff base reaction of compound (1) with p-nitrobenzaldehyde. Synthesis of compound (1) is described in *Aust. J. Chem* (1994) 47, 143–179. A copper complex of (1) is dissolved in dry ethanol (2.4 mmoles in 100 mls) and p-nitrobenzaldehyde (2.2 mmoles) is added. The reaction mixture is evaporated to dryness and reconstituted (with dry ethanol) twice to remove any water. The reaction mixture is once again reconstituted in dry ethanol and stirred for 30 mins under nitrogen gas. Sodium cyanoborohydride (25 mmoles), glacial acetic acid (2 mmoles) and activated 3 Å molecular sieves are added and the reaction is allowed to stir overnight. The mixture is filtered, evaporated to dryness and extracted with chloroform and water (100 ml:200 ml). The water layer is diluted to 2 L, sorbed onto SP Sephadex C25 and eluted with 0.3 M sodium acetate. (Scheme 1).

B. Preparation of Compound (3)

To palladium/C catalyst (20 mg) in water (0.5 ml) is added sodium borohydride (50 mg) in water (0.5 ml) under nitrogen gas. To this mixture is then added compound (2) (30 mg) dissolved in approximately 0.1 M sodium hydroxide (0.5 ml). The mixture is left to stir at room temperature for a further 30 mins or until the solution becomes clear. A 2 ml glass vial is cooled on ice. The mixture is 0.22 μm filtered into the cooled vial to remove the suspended palladium/C catalyst. To this cooled filtrate is added concentrated hydrochloric acid dropwise until all excess sodium borohydride is quenched (i.e. until gas evolution on addition of acid ceases). The quantity of product is determined by titration with a known concentration of $^{64}$Cu as described in Example 2. Product is stored frozen at pH <1 in a rubber-stoppered vial under nitrogen gas. Yield: >95% (Scheme 2). The final product is characterised by $^1$H-NMR in D$_2$O at 298K (Bruker Avance DPX 400). $^1$H NMR 3.28 ppm, m, 6H, CH$_2$ (cage); 3.39 ppm, m, 6H, CH$_2$ (cage); 3.59 ppm, s, 6H, CH$_2$ (cage); 3.71 ppm, s, 6H, CH$_2$ (cage); 4.45 ppm, s, 2H, CH$_2$; 7.51 ppm, d, 2H, Ar; 7.70 ppm, d, 2H, Ar.

Example 2

Complexation of $^{64}$Cu by Compound (3)

The effect of pH on complexation of $^{64}$Cu by compound (3) was investigated. Compound (3) was diluted into buffers of pH 3.0, 4.0, 5.0, 6.0, 7.0, 8.0 and 9.0. A sufficient amount of $^{64}$Cu was added and the rate of complexation was monitored at (t=1, 2.5, 5, 10, 60 and 90 mins) (see method below) by Instant Thin Layer Chromatography (ITLC-SG). Complete complexation (>98%) was achieved within 1 min for all pH ≧4.0. The rate of complexation at pH 3.0 was slower. (FIG. 2).

Monitoring Complexation by ITLC-SG

ITLC-SG strips (10 cm×0.8 cm) were spotted with ~1 μL of reaction mixture 1 cm from the bottom of the strip (origin) and were developed in a solvent containing 0.1 M sodium acetate (pH 4.5): ethanol=9:1. $^{64}$Cu-compound (3) remains at the origin (R$_f$=0.0), and "free" $^{64}$Cu appears at the solvent front (R$_f$=1.0).

A typical method of radiolabelling the ligand is achieved by adjusting the pH of an aqueous solution of the ligand to pH 5.0. Sufficient volume of $^{64/67}$Cu solution (usually in 0.02 M HCl or diluted into 0.1 M sodium acetate buffer pH 5.0) is added to form a 1:1 complex. The efficacy of labelling is determined by ITLC-SG as described above. One main radiochemical species is observed.

Example 3

Serum Stability of $^{67}$Cu Complex of Compound (4)

Serum stability studies were conducted by incubating a $^{67}$Cu complex of related species (4) in human plasma at 37° C.

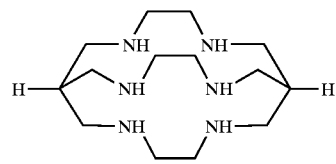

[4]

At various time intervals, the complex was separated from the plasma by size exclusion chromatography and the complex breakdown was assessed. Results indicated that no more than 2% of the copper is lost from the chelator during the first 174 hours at 37° C. (FIGS. 1a and 1b).

Example 4

Synthesis of B72.3 Conjugated with (3) Using 1-Ethyl-3-(3-dimethylamino-propyl)carbodiimide (EDC)

A typical method for radiolabelling an antibody (such as B72.3) is to incubate the antibody with the ligand (such as compound (3)) in the presence of EDC at pH 5.0 for 30 mins at 37° C. The unreacted ligand and EDC by-products are removed by washing with in buffer (pH 5.0) on a size exclusion ultra filtration membrane. The purified immunoconjugate is exposed to a slight excess of $^{64/67}$Cu. The reaction is allowed to proceed at room temperature, and labelling is complete in less than 5 mins. Excess $^{64/67}$Cu is removed by washing with 0.1 M EDTA in PBS (pH 7.2) on a size exclusion ultra filtration membrane or by separation on a size exclusion column (sephadex G25, eluted with PBS pH 7.2). (Scheme 3).

The conditions for radiolabelling B72.3 were optimised over incubation time (30 mins), reaction pH (5.0), concentration of B72.3 (5 mg/ml) and the molar ratio of B72.3:EDC:ligand (1:1000:250).

Scheme 3
Synthesis of protein conjugated with compound (3) using EDC

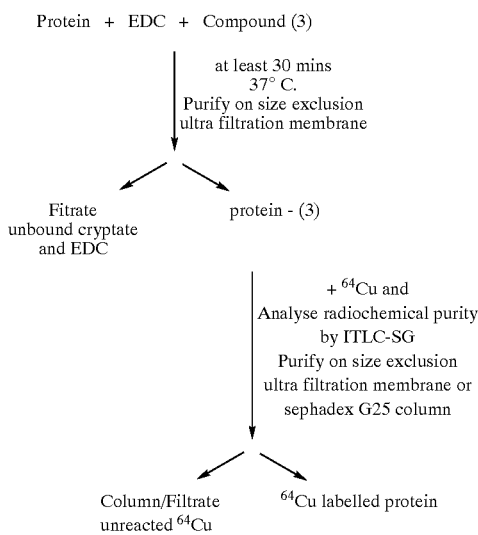

Figure 3:
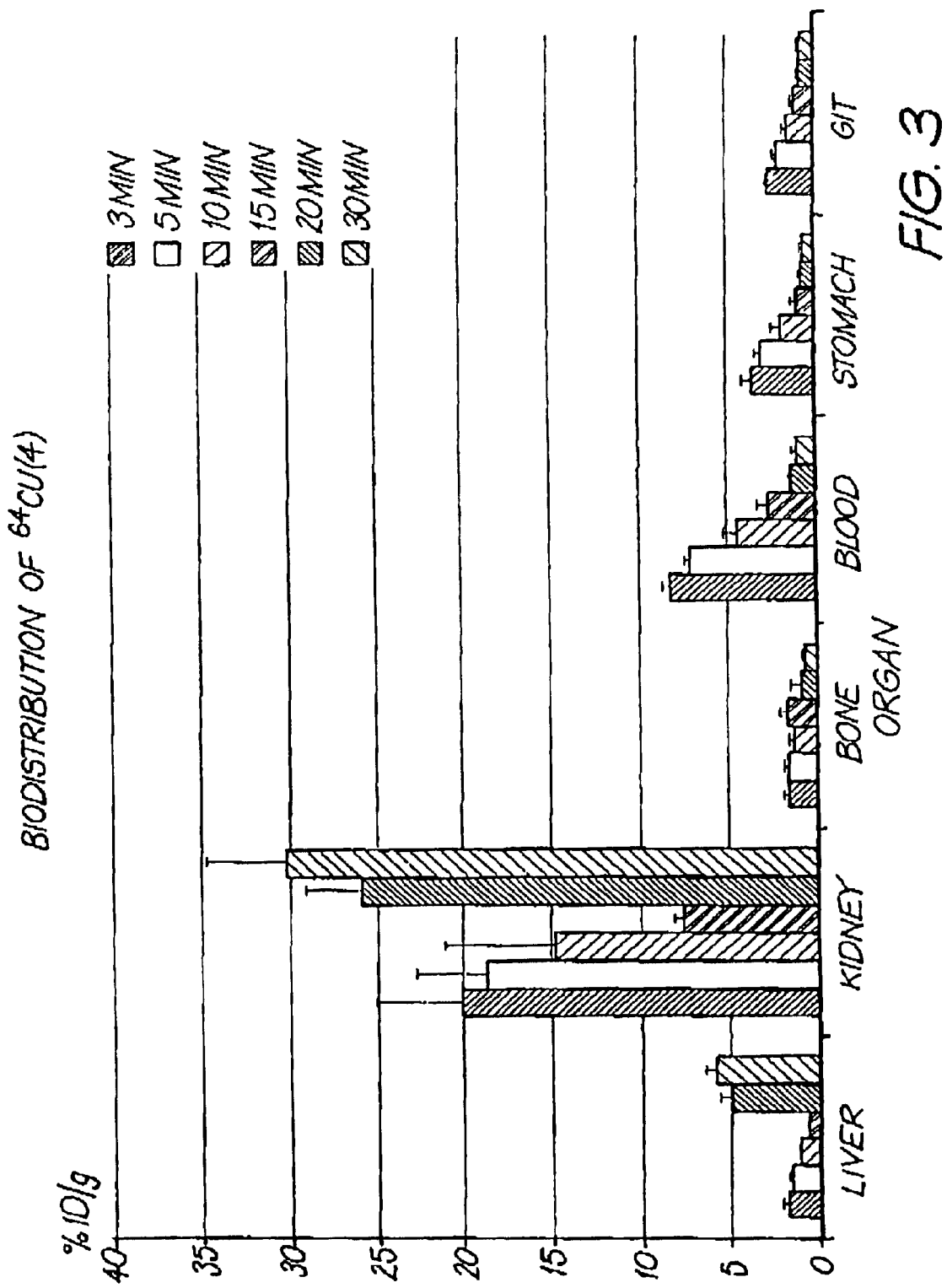
FIG. 3 is a graphical representation of the biodistribution of a $^{64}$Cu complex of compound (4)
Figure 4:
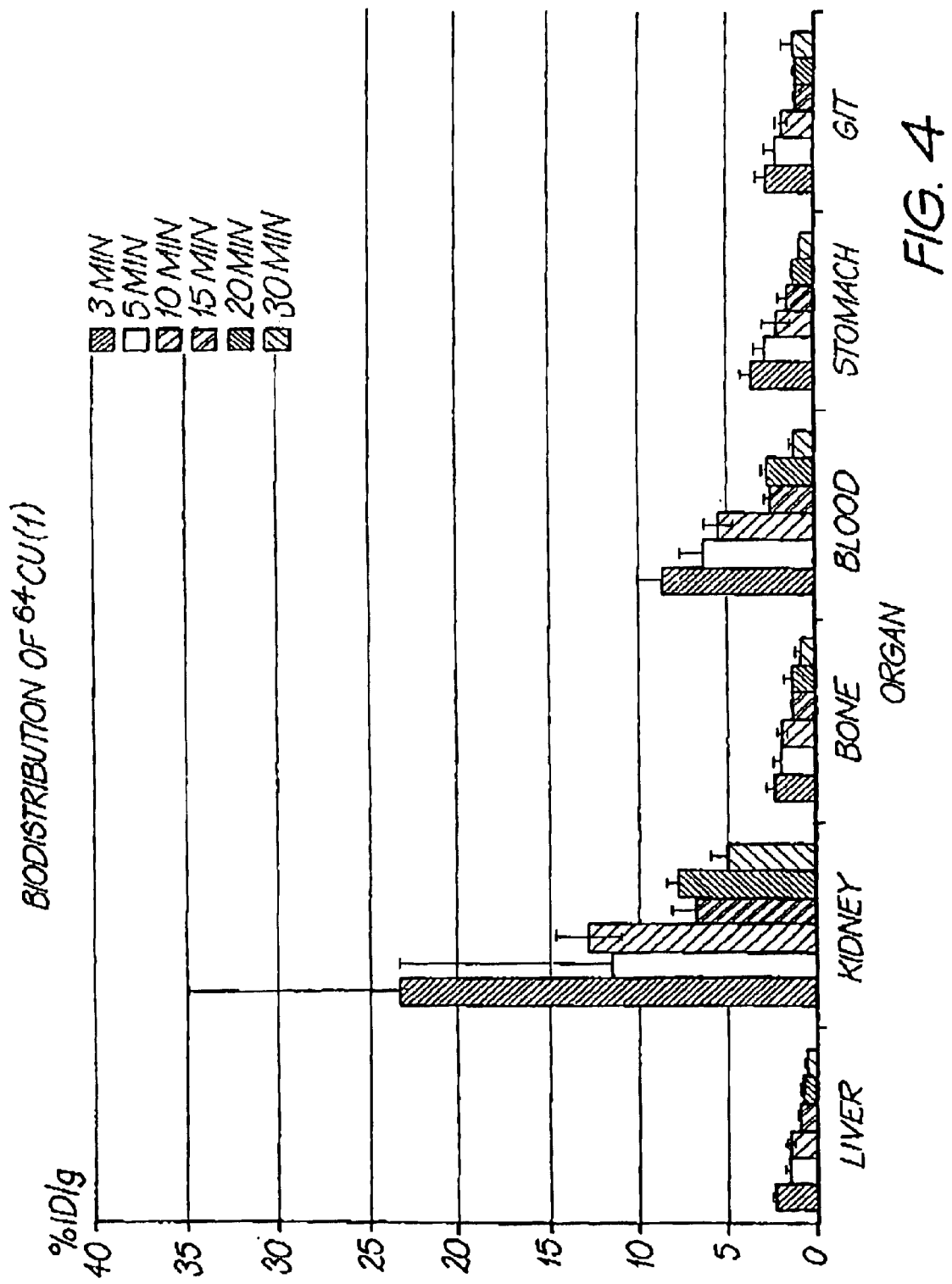
FIG. 4 is a graphical representation of the biodistribution of a $^{64}$Cu complex of compound (1)
Figure 5:
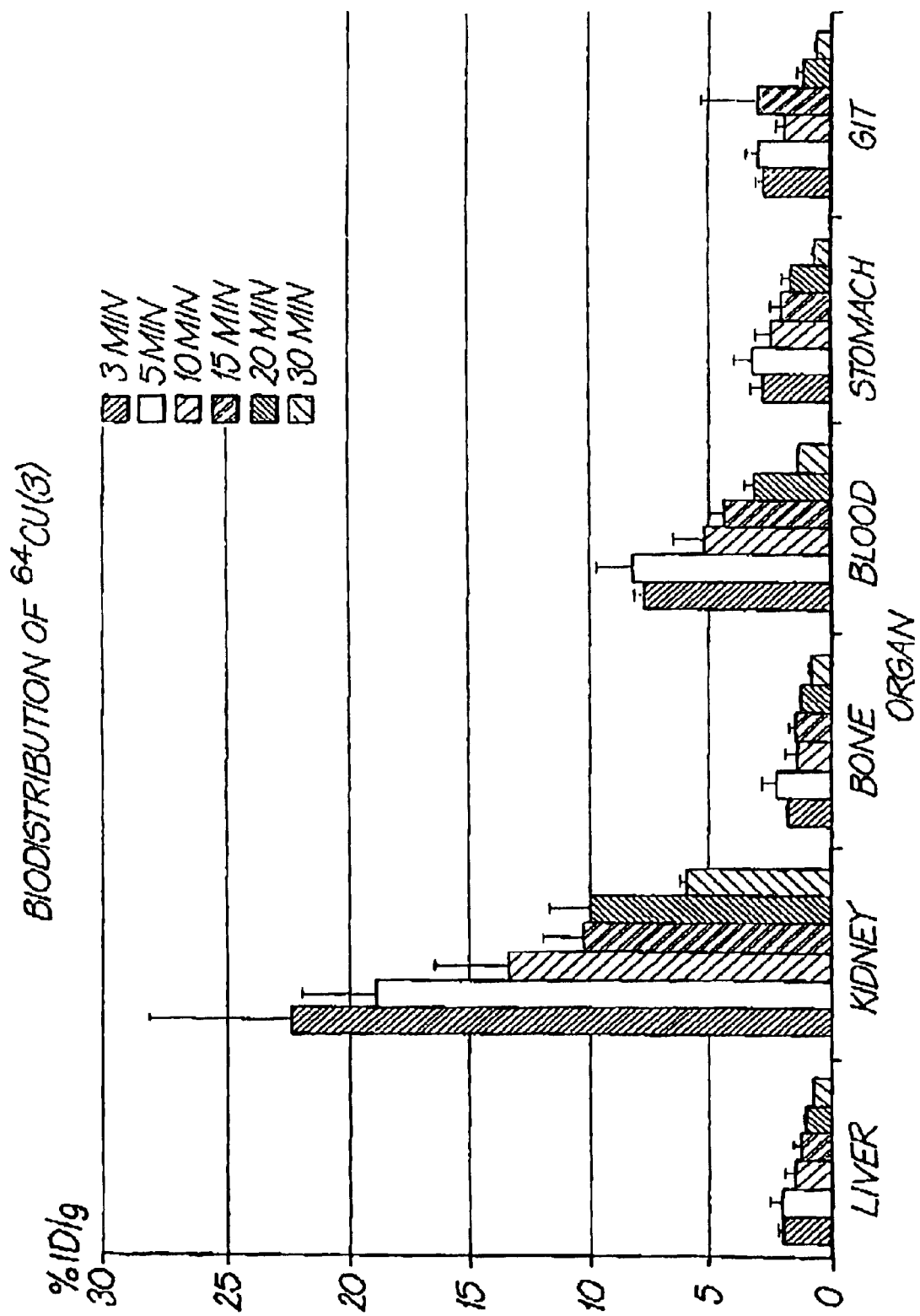
FIG. 5 is a graphical representation of the biodistribution of a $^{64}$Cu complex of compound (3)

Example 5
Biodistribution of Cu Complexes of (1), (3) and (4) in Balb/C Mice The biodistribution of the $^{64}$Cu complexes of compounds (1), (3) and (4) (0.10 ml intravenous injection) were evaluated in balb/c mice (5 animals per time point) at 3, 5, 10, 15, 20 and 30 minute time intervals. Biodistribution studies were performed in duplicate. Biodistribution of the radiolabel is presented in Tables 1, 2 and 3, and is illustrated diagrammatically in FIGS. 3, 4 and 5.

Example 6
Evaluation of $^{64}$Cu-Labelled Conjugate of B72.3 with Compound (3) in Tumour Bearing Nude Mice The B72.3 antibody recognises the TAG-72 antigen which is expressed on colorectal and ovarian tumours. The animal model used in the present study uses LS174t cells which also express TAG-72 antigen. The biodistribution of the $^{64}$Cu immunoconjugate (0.10 ml intravenous injection) was evaluated in LS174t tumour bearing nude mice (5 animals per time point) at 1, 3, 5, 24 and 48 hour time intervals. Biodistribution studies were performed in duplicate. Biodistribution of the radiolabel is presented in Table 4, and is illustrated diagrammatically in FIG. 6a; Biodistribution of complex of compounds (1) (2) and (3) show that if the ligand actually detaches from the antibody in any form it will clear rapidly from the system and not release the $^{64}$Cu.

TABLE 1

$^{64}$Cu-labelled compound (4)
% INJECTED DOSE PER GRAM

| | TIME | | | | | | | | | | | |
|---|---|---|---|---|---|---|---|---|---|---|---|---|
| | 3 MIN | | 5 MIN | | 10 MIN | | 15 MIN | | 20 MIN | | 30 MIN | |
| ORGAN | MEAN | S.D. | MEAN | S.D. | MEAN | S.D. | MEAN | S.D. | MEAN | S.D. | MEAN | S.D. |
| LIVER | 1.81 | 0.30 | 1.59 | 0.12 | 1.16 | 0.06 | 0.64 | 0.06 | 5.01 | 0.55 | 5.76 | 0.58 |
| SPLEEN | 2.26 | 0.43 | 2.17 | 0.29 | 1.28 | 0.14 | 0.67 | 0.15 | 0.52 | 0.08 | 0.35 | 0.07 |
| KIDNEY | 20.08 | 4.98 | 18.62 | 4.09 | 14.79 | 6.26 | 7.52 | 0.54 | 25.99 | 3.24 | 30.26 | 4.50 |
| MUSCLE | 1.76 | 0.23 | 2.10 | 0.59 | 1.24 | 0.27 | 1.73 | 1.32 | 0.36 | 0.06 | 1.27 | 1.43 |
| SKIN | 5.98 | 0.31 | 6.46 | 0.56 | 4.21 | 0.68 | 2.76 | 0.10 | 1.73 | 0.45 | 1.42 | 0.42 |
| BONE | 1.60 | 0.25 | 1.56 | 0.24 | 1.28 | 0.23 | 1.60 | 0.41 | 0.89 | 0.51 | 0.65 | 0.10 |
| LUNGS | 5.85 | 0.03 | 5.28 | 0.46 | 2.84 | 1.09 | 2.09 | 0.24 | 1.13 | 0.30 | 0.92 | 0.15 |
| HEART | 3.25 | 0.34 | 2.66 | 0.14 | 1.60 | 0.36 | 1.08 | 0.18 | 0.51 | 0.08 | 0.47 | 0.17 |
| BLOOD | 8.25 | 0.32 | 7.08 | 0.22 | 4.41 | 0.78 | 2.71 | 0.57 | 1.40 | 0.12 | 1.07 | 0.21 |
| BLADDER | 13.15 | 6.81 | 28.05 | 18.33 | 69.91 | 54.03 | 8.17 | 4.96 | 16.38 | 20.77 | 25.38 | 35.78 |
| STOMACH | 3.53 | 0.56 | 3.04 | 0.29 | 1.84 | 0.55 | 0.89 | 0.37 | 0.70 | 0.14 | 0.65 | 0.10 |
| GIT | 2.62 | 0.08 | 2.16 | 0.20 | 1.49 | 0.31 | 1.07 | 0.18 | 0.89 | 0.05 | 0.80 | 0.04 |

TABLE 2

$^{64}$Cu-labelled compound (1)
% INJECTED DOSE PER GRAM

| | TIME | | | | | | | | | | | |
|---|---|---|---|---|---|---|---|---|---|---|---|---|
| | 3 MIN | | 5 MIN | | 10 MIN | | 15 MIN | | 20 MIN | | 30 MIN | |
| ORGAN | MEAN | S.D. | MEAN | S.D. | MEAN | S.D. | MEAN | S.D. | MEAN | S.D. | MEAN | S.D. |
| LIVER | 2.29 | 0.22 | 1.50 | 0.17 | 1.42 | 0.22 | 0.82 | 0.19 | 0.69 | 0.15 | 0.50 | 0.08 |
| SPLEEN | 2.09 | 0.52 | 1.48 | 0.21 | 1.54 | 0.25 | 1.44 | 0.76 | 0.69 | 0.12 | 0.52 | 0.16 |
| KIDNEY | 23.18 | 11.73 | 11.50 | 1.34 | 12.80 | 1.83 | 6.77 | 1.40 | 7.77 | 0.67 | 4.95 | 0.92 |
| MUSCLE | 1.81 | 0.32 | 1.81 | 0.59 | 2.39 | 1.14 | 2.28 | 1.66 | 1.17 | 1.02 | 1.33 | 1.59 |
| SKIN | 5.82 | 0.42 | 5.59 | 0.59 | 5.48 | 1.07 | 2.61 | 0.44 | 2.96 | 0.72 | 1.63 | 0.08 |
| BONE | 2.25 | 0.45 | 1.87 | 0.47 | 1.79 | 0.29 | 1.23 | 0.12 | 1.25 | 0.44 | 0.78 | 0.23 |
| LUNGS | 6.51 | 1.28 | 4.45 | 0.54 | 3.91 | 1.98 | 2.06 | 0.32 | 2.73 | 0.61 | 0.85 | 0.31 |
| HEART | 3.11 | 0.38 | 2.25 | 0.10 | 2.27 | 0.43 | 0.89 | 0.12 | 1.23 | 0.71 | 0.40 | 0.10 |
| BLOOD | 8.68 | 1.35 | 6.32 | 0.70 | 5.45 | 0.81 | 2.48 | 0.31 | 2.63 | 0.29 | 1.14 | 0.25 |
| BLADDER | 24.36 | 16.90 | 31.12 | 19.21 | 27.75 | 21.59 | 15.17 | 8.53 | 23.29 | 15.56 | 122.93 | 71.11 |
| STOMACH | 3.50 | 0.64 | 2.73 | 0.36 | 2.08 | 0.80 | 1.50 | 0.46 | 1.16 | 0.06 | 0.74 | 0.04 |
| GIT | 2.75 | 0.59 | 2.21 | 0.08 | 1.85 | 0.38 | 1.11 | 0.06 | 1.05 | 0.17 | 1.16 | 0.72 |

TABLE 3

$^{64}$Cu-labelled compound (3)
% INJECTED DOSE PER GRAM

| | TIME | | | | | | | | | | | |
|---|---|---|---|---|---|---|---|---|---|---|---|---|
| | 3 MIN | | 5 MIN | | 10 MIN | | 15 MIN | | 20 MIN | | 30 MIN | |
| ORGAN | MEAN | S.D. | MEAN | S.D. | MEAN | S.D. | MEAN | S.D. | MEAN | S.D. | MEAN | S.D. |
| LIVER | 1.94 | 0.17 | 2.00 | 0.52 | 1.46 | 0.39 | 1.24 | 0.23 | 1.04 | 0.08 | 0.72 | 0.02 |
| SPLEEN | 1.96 | 0.14 | 2.01 | 0.16 | 1.26 | 0.20 | 1.09 | 0.25 | 0.93 | 0.13 | 0.39 | 0.05 |
| KIDNEY | 22.41 | 5.77 | 18.99 | 2.98 | 13.41 | 3.04 | 10.26 | 1.76 | 9.98 | 1.73 | 5.95 | 0.27 |
| MUSCLE | 1.98 | 0.48 | 3.17 | 2.34 | 1.73 | 0.28 | 2.40 | 1.39 | 2.13 | 1.35 | 0.50 | 0.01 |
| SKIN | 5.63 | 1.05 | 6.18 | 1.17 | 4.86 | 1.14 | 4.49 | 1.03 | 3.41 | 1.10 | 1.45 | 0.13 |
| BONE | 1.68 | 0.04 | 2.11 | 0.60 | 1.29 | 0.43 | 1.36 | 0.24 | 1.11 | 0.08 | 0.72 | 0.10 |
| LUNGS | 5.48 | 0.61 | 5.74 | 1.07 | 4.00 | 0.79 | 3.25 | 0.64 | 2.59 | 0.50 | 1.13 | 0.01 |
| HEART | 2.79 | 0.36 | 3.00 | 0.59 | 2.03 | 0.58 | 1.56 | 0.29 | 1.24 | 0.05 | 0.50 | 0.11 |
| BLOOD | 7.74 | 0.43 | 8.19 | 1.53 | 5.23 | 1.28 | 4.39 | 0.59 | 3.05 | 0.44 | 1.25 | 0.02 |
| BLADDER | 11.36 | 4.02 | 12.31 | 4.09 | 14.36 | 9.79 | 10.54 | 9.64 | 13.45 | 16.47 | 2.74 | 2.02 |
| STOMACH | 2.69 | 0.51 | 3.11 | 0.79 | 2.35 | 0.65 | 1.91 | 0.45 | 1.54 | 0.33 | 0.60 | 0.04 |
| GIT | 2.66 | 0.29 | 2.88 | 0.46 | 1.80 | 0.38 | 2.92 | 2.46 | 1.05 | 0.22 | 0.55 | 0.03 |

TABLE 4

$^{64}$Cu-labelled conjugate of B72.3 with compound (3)
% INJECTED DOSE PER GRAM

| | TIME | | | | | | | | | | | |
|---|---|---|---|---|---|---|---|---|---|---|---|---|
| | 1 HR | | 3 HR | | 5 HR | | 16 HR | | 24 HR | | 48 HR | |
| ORGAN | MEAN | S.D. | MEAN | S.D. | MEAN | S.D. | MEAN | S.D. | MEAN | S.D. | MEAN | S.D. |
| LIVER | 19.09 | 1.05 | 18.44 | 0.58 | 19.54 | 2.34 | 16.38 | 1.59 | 15.52 | 2.95 | 13.76 | 3.21 |
| SPLEEN | 11.51 | 1.13 | 8.35 | 1.19 | 10.17 | 0.98 | 10.08 | 1.75 | 8.47 | 1.89 | 8.44 | 1.57 |
| KIDNEY | 10.64 | 1.47 | 9.94 | 0.15 | 10.41 | 1.10 | 9.16 | 1.77 | 7.39 | 0.65 | 7.59 | 1.35 |
| MUSCLE | 1.45 | 0.52 | 1.48 | 0.23 | 1.45 | 0.16 | 1.98 | 0.27 | 2.54 | 0.54 | 1.72 | 0.42 |
| SKIN | 2.83 | 0.52 | 5.18 | 0.26 | 5.99 | 1.38 | 8.64 | 1.16 | 8.30 | 1.30 | 6.95 | 0.16 |
| BONE | 4.42 | 0.55 | 3.82 | 0.49 | 3.21 | 0.30 | 3.93 | 0.49 | 4.28 | 0.72 | 3.39 | 0.38 |
| LUNGS | 13.32 | 1.52 | 11.43 | 1.44 | 9.78 | 0.86 | 11.03 | 1.93 | 7.76 | 0.87 | 6.81 | 1.09 |
| HEART | 10.56 | 2.29 | 8.58 | 1.21 | 9.04 | 3.30 | 6.77 | 0.92 | 5.14 | 0.72 | 5.20 | 0.43 |
| BLOOD | 47.98 | 5.60 | 37.94 | 1.52 | 33.41 | 3.66 | 26.41 | 1.48 | 21.50 | 1.81 | 18.69 | 2.01 |
| BLADDER | 2.33 | 0.77 | 2.93 | 0.62 | 3.15 | 0.47 | 7.00 | 5.09 | 5.41 | 2.37 | 4.87 | 0.92 |
| STOMACH | 1.41 | 0.29 | 1.69 | 0.33 | 2.32 | 0.51 | 1.48 | 0.74 | 1.58 | 0.31 | 1.43 | 0.32 |
| GIT | 2.23 | 0.35 | 2.60 | 0.20 | 2.87 | 0.23 | 2.28 | 0.14 | 2.20 | 0.20 | 1.86 | 0.31 |
| TAIL | 5.03 | 0.73 | 4.96 | 0.83 | 5.64 | 1.82 | 6.14 | 2.47 | 5.18 | 1.20 | 4.08 | 0.30 |
| TUMOUR | 5.98 | 0.80 | 11.10 | 0.76 | 12.31 | 1.68 | 23.77 | 2.46 | 29.43 | 4.44 | 38.43 | 4.79 |

TABLE 5

Biodistribution of $^{123}$I-B72.3 in nu/nu mice

| % ID/g Time (hours) | 1 | | 3 | | 6 | | 16 | | 24 | | 48 | |
|---|---|---|---|---|---|---|---|---|---|---|---|---|
| ORGAN | Mean | SD | Mean | SD | Mean | SD | Mean | SD | Mean | SD | Mean | SD |
| LIVER | 11.89 | 2.33 | 8.93 | 1.24 | 7.45 | 1.51 | 5.61 | 0.64 | 5.03 | 0.82 | 4.92 | 0.90 |
| SPLEEN | 10.17 | 2.79 | 6.92 | 0.92 | 6.27 | 0.79 | 5.20 | 0.95 | 4.33 | 1.34 | 4.58 | 1.25 |
| KIDNEY | 11.20 | 0.77 | 8.89 | 1.40 | 9.24 | 0.53 | 5.83 | 0.88 | 5.40 | 0.98 | 4.76 | 0.78 |
| MUSCLE | 1.69 | 0.42 | 2.40 | 0.43 | 3.04 | 0.59 | 2.55 | 0.65 | 2.70 | 0.42 | 2.48 | 0.33 |
| SKIN | 4.36 | 1.85 | 5.96 | 0.94 | 7.79 | 0.76 | 7.94 | 0.95 | 7.96 | 0.78 | 7.41 | 1.44 |
| BONE | 5.43 | 0.54 | 4.43 | 0.69 | 3.23 | 0.43 | 3.19 | 0.78 | 2.58 | 0.58 | 2.54 | 0.36 |
| LUNGS | 14.28 | 2.97 | 12.84 | 2.89 | 11.00 | 1.57 | 7.39 | 1.62 | 6.64 | 1.57 | 6.47 | 0.64 |
| HEART | 14.03 | 6.26 | 10.11 | 1.16 | 9.46 | 1.59 | 7.28 | 2.50 | 5.78 | 0.62 | 4.87 | 1.10 |
| BLOOD | 55.63 | 3.36 | 44.78 | 4.03 | 42.20 | 3.93 | 28.27 | 3.00 | 28.73 | 2.23 | 22.73 | 2.50 |
| URINE | 3.96 | 0.58 | 13.29 | 5.00 | 18.31 | 6.92 | 7.28 | 4.17 | 6.92 | 1.11 | 6.87 | 2.11 |
| BLADDER | 3.49 | 1.15 | 5.10 | 1.63 | 4.85 | 0.91 | 4.74 | 1.24 | 5.70 | 1.13 | 6.63 | 1.23 |
| STOMACH | 1.80 | 0.23 | 2.94 | 0.44 | 4.06 | 0.50 | 2.64 | 0.90 | 3.06 | 0.99 | 3.05 | 0.72 |
| GIT | 2.35 | 0.26 | 2.74 | 0.29 | 2.74 | 0.39 | 1.84 | 0.33 | 1.65 | 0.26 | 1.51 | 0.07 |
| THYROID | 8.76 | 3.60 | 17.29 | 6.24 | 38.66 | 7.92 | 29.47 | 9.54 | 85.96 | 44.73 | 549.83 | 353.44 |
| TUMOUR | 9.61 | 2.04 | 16.46 | 1.61 | 31.43 | 8.39 | 31.37 | 6.54 | 44.67 | 8.50 | 46.17 | 7.25 |
| % ID THYROID | 0.08 | 0.02 | 0.19 | 0.03 | 0.42 | 0.11 | 0.40 | 0.18 | 1.24 | 0.64 | 2.59 | 1.13 |
| TUMOUR:BLOOD | 0.2 | 0.0 | 0.4 | 0.1 | 0.7 | 0.3 | 1.1 | 0.3 | 1.6 | 0.4 | 2.0 | 0.5 |
| TUMOUR:LIVER | 0.8 | 0.3 | 1.8 | 0.4 | 4.2 | 2.0 | 5.6 | 1.8 | 8.9 | 3.1 | 9.4 | 3.2 |

TABLE 5-continued

Biodistribution of $^{123}$I-B72.3 in nu/nu mice

| % ID/g Time (hours) ORGAN | 1 Mean | SD | 3 Mean | SD | 6 Mean | SD | 16 Mean | SD | 24 Mean | SD | 48 Mean | SD |
|---|---|---|---|---|---|---|---|---|---|---|---|---|
| TUMOUR:KIDNEY | 0.9 | 0.2 | 1.9 | 0.5 | 3.4 | 1.1 | 5.4 | 1.9 | 8.3 | 3.1 | 9.7 | 3.1 |
| KIDNEY:BLOOD | 0.2 | 0.0 | 0.2 | 0.0 | 0.2 | 0.0 | 0.2 | 0.1 | 0.2 | 0.0 | 0.2 | 0.1 |
| KIDNEY:LIVER | 0.9 | 0.2 | 1.0 | 0.3 | 1.2 | 0.3 | 1.0 | 0.3 | 1.1 | 0.4 | 1.0 | 0.3 |

TABLE 6

Biodistribution of $^{111}$In-DTPA-B72.3 in nu/nu mice.

| % ID/g Time (hours) ORGAN | 1 Mean | SD | 3 Mean | SD | 6 Mean | SD | 16 Mean | SD | 24 Mean | SD | 48 Mean | SD |
|---|---|---|---|---|---|---|---|---|---|---|---|---|
| LIVER | 13.4 | 1.72 | 10.54 | 1.41 | 11.2 | 1.2 | 7.27 | 0.86 | 8.43 | 2.28 | 7.59 | 0.72 |
| SPLEEN | 12.52 | 2.66 | 9.56 | 1.96 | 10.05 | 2.55 | 6.47 | 3.33 | 7.32 | 1.43 | 4.48 | 2.28 |
| KIDNEY | 15.41 | 1.57 | 12.04 | 1.67 | 14.13 | 1.83 | 15.59 | 1.39 | 13.97 | 1.64 | 15.04 | 1.57 |
| MUSCLE | 2.08 | 0.81 | 1.96 | 0.42 | 2.56 | 0.32 | 2.44 | 0.82 | 2.28 | 0.26 | 1.84 | 0.51 |
| SKIN | 4.17 | 1.98 | 7.54 | 1.53 | 9.31 | 1.41 | 9.48 | 1.21 | 8.44 | 0.42 | 7.54 | 0.75 |
| BONE | 5.9 | 1.12 | 4.59 | 0.53 | 3.85 | 0.97 | 5.81 | 1.12 | 5.52 | 0.58 | 5.23 | 0.9 |
| LUNGS | 18.58 | 4.72 | 13.14 | 4.58 | 13.03 | 2.65 | 8.06 | 1.89 | 6.58 | 1.4 | 7.07 | 1.93 |
| HEART | 11.9 | 3.88 | 9.59 | 1.65 | 11.71 | 4.12 | 6.25 | 0.88 | 4.99 | 0.39 | 3.95 | 0.45 |
| BLOOD | 56.19 | 9.04 | 39.03 | 4.66 | 38.23 | 3.64 | 26.51 | 1.72 | 21.78 | 2.36 | 17.04 | 0.89 |
| URINE | | | 5.23 | 0 | 3.96 | 1.16 | 4.46 | 1.68 | 4.46 | 1.12 | 4.43 | 1.56 |
| BLADDER | 11.82 | 9.4 | 5.59 | 2.85 | 8.31 | 19.94 | 7.68 | 2.97 | 6.88 | 1.87 | 4.28 | 0.39 |
| STOMACH | 2.43 | 0.8 | 2.49 | 0.66 | 2.2 | 0.9 | 1.53 | 0.48 | 1.47 | 0.46 | 1.47 | 0.44 |
| GIT | 2.12 | 0.34 | 2.44 | 0.51 | 2.33 | 0.42 | 2.17 | 0.25 | 2.04 | 0.2 | 2.33 | 0.2 |
| TAIL | 9.37 | 5.68 | 8.39 | 4.38 | 8.53 | 5.27 | 4.98 | 1.17 | 4.69 | 0.96 | 3.79 | 1.37 |
| THYROID | 18.66 | 8.1 | 25.91 | 17.2 | 8.09 | 3.14 | 7.37 | 1.62 | 8.51 | 2.21 | 4.45 | 0.91 |
| TUMOUR | 8.87 | 2.39 | 17.95 | 4.93 | 21.24 | 6.11 | 38.25 | 8.71 | 35 | 5.21 | 48.99 | 4 |
| % ID THYROID | 0.07 | 0.01 | 0.06 | 0.03 | 0.07 | 0.01 | 0.07 | 0.02 | 0.06 | 0.03 | 0.06 | 0.01 |
| TUMOUR:BLOOD | 0.2 | 0.1 | 0.5 | 0.2 | 0.6 | 0.2 | 1.4 | 0.4 | 1.6 | 0.4 | 2.9 | 0.4 |
| TUMOUR:LIVER | 0.7 | 0.3 | 1.7 | 0.7 | 1.9 | 0.7 | 5.3 | 1.8 | 4.2 | 1.7 | 6.5 | 1.1 |
| TUMOUR:KIDNEY | 0.6 | 0.2 | 1.5 | 0.6 | 1.5 | 0.6 | 2.5 | 0.8 | 2.5 | 0.7 | 3.3 | 0.6 |
| KIDNEY:BLOOD | 0.3 | 0.1 | 0.3 | 0.1 | 0.4 | 0.1 | 0.6 | 0.1 | 0.6 | 0.1 | 0.9 | 0.1 |
| KIDNEY:LIVER | 1.2 | 0.3 | 1.1 | 0.3 | 1.3 | 0.3 | 2.1 | 0.4 | 1.7 | 0.6 | 2.0 | 0.4 |

It is to be understood that the term "SarAr" as used in the following tables and description refers to compound (3) as shown in example 1.

TABLE 7

Maximum Radiation Dose Estimates for $^{64}$Cu-SarAr-B72.3

| Organ | Total Dose mGy/MBq | Total Dose Rad/mCi |
|---|---|---|
| Adrenals | 0.030 | 0.111 |
| Brain | 0.018 | 0.068 |
| Breasts | 0.021 | 0.078 |
| Gallbladder Wall | 0.036 | 0.133 |
| LLI Wall | 0.094 | 0.347 |
| Small Intestine | 0.047 | 0.175 |
| Stomach | 0.029 | 0.107 |
| ULI Wall | 0.069 | 0.255 |
| Heart Wall | 0.075 | 0.278 |
| Kidneys | 0.129 | 0.477 |
| Liver | 0.152 | 0.563 |
| Lungs | 0.062 | 0.230 |
| Ovaries | 0.026 | 0.095 |
| Muscle | 0.013 | 0.047 |
| Pancreas | 0.030 | 0.110 |
| Red Marrow | 0.029 | 0.107 |
| Bone Surfaces | 0.030 | 0.111 |
| Skin | 0.019 | 0.069 |
| Spleen | 0.088 | 0.327 |
| Thymus | 0.023 | 0.086 |
| Testes | 0.019 | 0.072 |

TABLE 7-continued

Maximum Radiation Dose Estimates for $^{64}$Cu-SarAr-B72.3

| Thyroid | 0.020 | 0.074 |
|---|---|---|
| Bladder Wall | 0.019 | 0.070 |
| Uterus | 0.029 | 0.109 |
| Total Body | 0.024 | 0.090 |

| Tumour Mass (g) | S factor rad/uCi-h | Dose Gy | Dose rad |
|---|---|---|---|
| 0.1 | 2.25 | 17.80 | 1779.75 |
| 0.5 | 0.48 | 3.80 | 380.47 |
| 1.0 | 0.25 | 1.97 | 196.96 |
| 2.0 | 0.13 | 1.00 | 99.67 |

TABLE 8

Maximum Radiation Dose Estimate for $^{131}$I.B72.3

| Organ | Total Dose mGy/MBq | Total Dose rad/mCi |
|---|---|---|
| Adrenals | 0.821 | 3.038 |
| Brain | 0.514 | 1.902 |
| Breasts | 0.603 | 2.231 |
| Gallbladder Wall | 0.913 | 3.378 |
| LLI Wall | 2.24 | 8.288 |
| Small Intestine | 1.3 | 4.810 |

TABLE 8-continued

Maximum Radiation Dose Estimate for $^{131}$I.B72.3

| | | | |
|---|---|---|---|
| Stomach | | 1.15 | 4.255 |
| ULI Wall | | 1.69 | 6.253 |
| Heart Wall | | 1.82 | 6.734 |
| Kidneys | | 2.41 | 8.917 |
| Liver | | 1.92 | 7.104 |
| Lungs | | 1.55 | 5.735 |
| Muscle | | 0.473 | 1.750 |
| Ovaries | | 0.768 | 2.842 |
| Pancreas | | 0.858 | 3.175 |
| Red Marrow | | 0.783 | 2.897 |
| Bone Surfaces | | 0.678 | 2.509 |
| Skin | | 0.547 | 2.024 |
| Spleen | | 2.04 | 7.548 |
| Testes | | 0.595 | 2.202 |
| Thymus | | 0.717 | 2.653 |
| Thyroid | | 44.6 | 165.020 |
| Bladder Wall | | 0.755 | 2.794 |
| Uterus | | 1.13 | 4.181 |
| Total Body | | 0.715 | 2.646 |
| Effective Dose | 3.45 | mSv/MBq | 12.765 rem/mCi |
| (Tumour not included) | | | |

| Tumour Mass (g) | S factor | Dose per mCi Gy | rad |
|---|---|---|---|
| 0.1 | 3.6 | 982 | 98275 |
| 0.5 | 0.759 | 207 | 20720 |
| 1 | 0.393 | 107 | 10728 |
| 2 | 0.2 | 54 | 5460 |

Contribution to Organ Dose from Activity in Tumour
It is assumed that the tumour is a small source located in the lower trunk which will make a contribution to all other organ doses. So that the computer software program known as MIRDOSE3 can be used, the activity is assumed to be located in the ovaries.
The ovary dose given in above was calculated separately. It is not the tumour dose.
Bladder Residence Time—The activity excreted via the bladder is almost insignificant.
The total bladder and urine residence times in Table 5 was used as the urine activity in the dose calculation. No excretion model or assumed voiding time were used.

TABLE 9

Maximum Radiation Dose Estimates for $^{90}$Y

| Organ | Total Dose mGy/MBq | Total Dose rad/mCi |
|---|---|---|
| Adrenals | 0.57 | 2.109 |
| Brain | 0.57 | 2.109 |
| Breasts | 0.57 | 2.109 |
| Gallbladder Wall | 0.57 | 2.109 |
| LLI Wall | 3.47 | 12.839 |
| Small Intestine | 1.36 | 5.032 |
| Stomach | 0.709 | 2.623 |
| ULI Wall | 2.25 | 8.325 |
| Heart Wall | 1.8 | 6.660 |
| Kidneys | 7.87 | 29.119 |
| Liver | 2.89 | 10.693 |
| Lungs | 1.88 | 6.956 |
| Muscle | 0.232 | 0.858 |
| Ovaries | 0.57 | 2.109 |
| Pancreas | 0.57 | 2.109 |
| Red Marrow | 0.964 | 3.567 |
| Bone Surfaces | 1.03 | 3.811 |
| Skin | 0.57 | 2.109 |
| Spleen | 2.32 | 8.584 |
| Testes | 0.57 | 2.109 |
| Thymus | 0.57 | 2.109 |
| Thyroid | 1.72 | 6.364 |
| Bladder Wall | 0.444 | 1.643 |
| Uterus | 0.57 | 2.109 |
| Total Body | 0.645 | 2.387 |

| Tumour Mass (g) | S rad/uCi-h | Dose per mCi Gy | rad |
|---|---|---|---|
| 0.1 | 8.97 | 546 | 54585 |
| 0.5 | 2.51 | 152.7 | 15274 |
| 1 | 1.4 | 85.2 | 8519 |
| 2 | 0.758 | 46.1 | 4613 |

Contribution to Organ Dose from Activity in Tumour

It is assumed that the tumour is a small source located in the lower trunk which will make a contribution to all other organ doses. So that the computer software program known as MIRDOSE3 can be used, the activity is assumed to be located in the ovaries. The ovary dose given in above was calculated separately. It is not the tumour dose.

Bladder Residence Time: The activity excreted via the bladder is almost insignificant.

The total bladder and urine residence times in Table 5 was used as the urine activity in the dose calculation. No excretion model or assumed voiding time were used.

TABLE 10

Radiation Dose Estimates for $^{131}$I-B72.3 (7 days)

| Organ | Total Dose mGy/MBq | Total Dose rad/mCi |
|---|---|---|
| Adrenals | 0.377 | 1.395 |
| Brain | 0.24 | 0.888 |
| Breasts | 0.276 | 1.021 |
| Gallbladder Wall | 0.418 | 1.547 |
| LLI Wall | 1.02 | 3.774 |
| Small Intestine | 0.587 | 2.172 |
| Stomach | 0.52 | 1.924 |
| ULI Wall | 0.769 | 2.845 |
| Heart Wall | 0.863 | 3.193 |
| Kidneys | 1.13 | 4.181 |
| Liver | 0.888 | 3.286 |
| Lungs | 0.727 | 2.690 |
| Muscle | 0.212 | 0.784 |
| Ovaries | 0.35 | 1.295 |
| Pancreas | 0.393 | 1.454 |
| Red Marrow | 0.358 | 1.325 |
| Bone Surfaces | 0.309 | 1.143 |
| Skin | 0.25 | 0.925 |
| Spleen | 0.951 | 3.519 |
| Testes | 0.272 | 1.006 |
| Thymus | 0.328 | 1.214 |
| Thyroid | 17.8 | 65.860 |
| Bladder Wall | 0.338 | 1.251 |
| Uterus | 0.497 | 1.839 |
| Total Body | 0.323 | 1.195 |

| Tumour Mass (g) | Dose to 24 hour rad/mCi |
|---|---|
| 0.1 | 2991 |
| 0.5 | 631 |
| 1 | 327 |
| 2 | 166 |

TABLE 11

Radiation Dose Estimates for $^{90}$Y (7 days)

| Organ | Total Dose mGy/MBq | Total Dose rad/mCi |
|---|---|---|
| Adrenals | 0.5 | 1.850 |
| Brain | 0.365 | 1.351 |
| Breasts | 0.5 | 1.850 |
| Gallbladder Wall | 0.5 | 1.850 |
| LLI Wall | 2.87 | 10.619 |
| Small Intestine | 1.14 | 4.218 |
| Stomach | 0.603 | 2.231 |
| ULI Wall | 1.87 | 6.919 |
| Heart Wall | 1.53 | 5.661 |
| Kidneys | 6.5 | 24.050 |
| Liver | 2.41 | 8.917 |
| Lungs | 1.58 | 5.846 |
| Muscle | 0.194 | 0.718 |
| Ovaries | 0.4 | 1.480 |
| Pancreas | 0.5 | 1.850 |
| Red Marrow | 0.808 | 2.990 |
| Bone Surfaces | 0.858 | 3.175 |
| Skin | 0.5 | 1.850 |
| Spleen | 1.97 | 7.289 |
| Testes | 0.5 | 1.850 |
| Thymus | 0.5 | 1.850 |
| Thyroid | 1.43 | 5.291 |
| Bladder Wall | 0.38 | 1.406 |
| Uterus | 0.5 | 1.850 |
| Total Body | 0.546 | 2.020 |

| Tumour Mass (g) | rad/mCi at 24 hour |
|---|---|
| 0.1 | 6925 |
| 0.5 | 1938 |
| 1 | 1081 |
| 2 | 585 |

Radiotherapeutic Study

Radiotherapeutic Study was conducted in two parts.

Part A where the theoretical doses to target and non-target organs were calculated for the analogous radioimmunoconjugates.

Part B where the various radioactive levels of $^{64}$Cu—SarAr—B72.3 was injected into tumour bearing mice and the therapeutic effect of the product was monitored as an extension of animal survival time.

Radiotherapeutic Study—Part A

Biodistribution studies of $^{123}$I- and $^{111}$In-radiolabelled B72.3 were conducted in LS174t tumour bearing nude mice (see Table 5,6) Standard calculations were performed using computer software MIRDOSE 3 which was used to compare target to non-target dose of their analogous therapeutic counterparts ($^{90}$Y and $^{131}$I respectively) with $^{64}$Cu—SarAr—B72.3 (see Table 7,8,9).

Theoretical maximum accumulated dose (which is equivalent to 10 half life decay) for each radioimmunoconjugate was calculated. Total body dose for $^{64}$Cu—SarAr—B72.3 was significantly lower (0.09 rad/mCi) than analogous products ($^{131}$I—B72.3, 2.64 rad/mCi; Y—B72.3, 2.387 rad/mCi). Comparative maximum doses to tumours of various sizes was calculated. Doses for $^{131}$I- and $^{90}$Y—B72.3 appear to be better than for $^{64}$Cu—SarAr—B72.3. However, the lack of stability of the radioimmunoconjugate at the tumour site in real biological systems prevents the tumour from receiving the maximum accumulated dose.

Hence doses to target and non-target organs were re-calculated assuming the radioimmunoconjugates ($^{131}$I and $^{90}$Y) were stable for approximately 24 hours at the tumour site and the non-target organs were dosed for up to 7 days allowing for natural biological clearance. MIRDOSE 3 was used to re-calculate dose to various organs under these conditions (see Table 10,11). Most relevant resultant target to non-target ratios are given in Table 12.

TABLE 12

Ratio of Target:Non-Target Doses for each Radioimmunoconjugate

|  | $^{64}$Cu | $^{131}$I | $^{90}$Y |
|---|---|---|---|
| Tumour (0.1 g):Kidneys | 2094 | 716 | 288 |
| Tumour (0.1 g):Liver | 1795 | 906 | 776 |
| Total Body Dose for 7 days | 0.09 | 1.195 | 2.020 |

*MIRDOSE 3 was used to estimate human organ doses assuming the residence times in man are the same as the animal model. It is acknowledged that this affects the accuracy of the dose estimates.

Radiotherapeutic Study—Part B

In order to assess therapeutic effect of $^{64}$Cu, in a real biological system, nude mice bearing LS174t colorectal carcinoma were injected with various doses (0, 10, 20, 30, 40 MBq) of $^{64}$Cu—SarAr—B72.3.

Results are given in Table 13 and a typical profile of a study is given in FIG. 1. For all activity levels greater than 20 MBq a significant extension in mouse life was achieved. Experimental details follow.

TABLE 13

Extension of mouse life relative to $^{64}$Cu-SarAr-B72.3 - Part B

| Experiment | Survival[1] (Days) |
|---|---|
| Control[2] | 20–25 |
| 10 MBq | 30–35 |
| 20 MBq | 60–70 |
| 30 MBq | 40–45 |
| 40 MBq | 30–35 |

[1]Greater than 30% of animals;
[2]Greater than 50 control animals;

FIG. 1. Radiotherapeutic effect of 30 MBq of $^{64}$Cu—SarAr—B72.3 in tumour bearing mice.

Experimental for Radiotherapeutic Study—Part B

Animal model: LS174t tumour tissue from nude mice was transplanted into nude mice for each experiment.

Animal selection: Only animals bearing tumours 3.5–5.5 mm
  7 days post transplantation were selected for each study. Up to 10 animals per dose.

Injection: The product was injected into the nude mice on Day 7 after transplantation of tumour tissue.

Doses: Various activities of Cu-64-SarAr—B72.3 was injected into the mice. Control animals receive only antibody.

Monitoring of animals: Animals were monitored for changes in tumour size
  Animal mass
  Behavioural and physical abnormalities
  (e.g. movement/gait, food intake and hunching)
  (For any of the above characteristic, frequency of weighing increased)

Histology, Haematology and Biochemistry:
  Animals were sacrificed at pre-determined time points (2 days, 1, 2, 3, 4 weeks, 2, 3, 4, 5 and 6 months).

Radiotoxic effects were monitored.

(conducted by external pathologist of Department of Veterinary Anatomy and Pathology, University of Sydney)

Endpoint of the study:

1) Body weight loss >20%.
2) Rapid weight loss of >10% overnight.
3) Ulceration of tumour
4) Limitation of normal behaviour (e.g. ability to feed or drink).
5) Tumour size 10×10 mm (UK Cancer Council)

Example 7

In accordance with the description of the invention provided above specific preferred pharmaceutical compositions of the present invention may be prepared, and examples of which are provided below. The following specific formulations are to be construed as merely illustrative examples of formulations and not as a limitation of the scope of the present invention in any way.

A compound of Formula (I) may be administered alone, although it is preferable that it be administered as a pharmaceutical formulation.

Example 7(a)

Composition for Parenteral Administration

A pharmaceutical composition of the present invention for intramuscular injection could be prepared to contain 1 mL sterile isotonic saline, and 1 mg of compound of Formula (I).

Similarly, a pharmaceutical composition for intravenous infusion may comprise 250 ml of sterile Ringer's solution, and 5 mg of compound of Formula (I).

Example 7(b)

Injectable Parenteral Composition

A pharmaceutical composition of this invention in a form suitable for administration by injection may be prepared by mixing 1% by weight of compound of Formula (I) in 12% by volume propylene glycol and isotonic saline. The solution is sterilised by filtration.

Modifications and variations such as would be apparent to a skilled addressee are deemed to be within the scope of the present invention. It is to be understood that the present invention should not be limited to the particular embodiment(s) described above. Throughout the specification, unless the context clearly indicates otherwise, the word, "comprise", "comprises", "comprising" or other variations thereof shall be understood as meaning that the stated integer is included and does not exclude other integers from being present even though those other integers are not explicitly stated.

Further, the present invention relates to all steps, compounds, intermediates as well as final products.

What is claimed is:

1. A compound which is capable of being radiolabelled of general Formula (I):

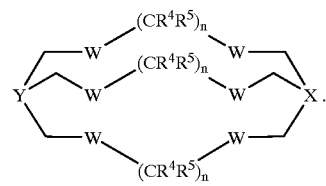

in which n represents an integer from 2 to 4, where each $R^4$ and $R^5$ is independently selected from —H, $CH_3$, COOH, $NO_2$, $CH_2OH$, $H_2PO_4$, $HSO_3$, CN, C(=O)$NH_2$ and CHO;

X and Y are the same or different and are selected from the group consisting of C—R, N, P and C—Z in which R is selected from hydrogen, halogen, hydroxyl, nitro, nitroso, amino, optionally substituted alkyl, optionally substituted aryl, optionally substituted aralkyl, cyano, —COOR', COCOOR', NH—CO$CH_2$Br, —NH—CO—CH=CH—COOR' in which R' is a hydrogen atom or alkyl group, wherein at least one of X and Y is C—Z;

W is selected from the group of NH, S and O; and

Z is a functionalised vinyl pyridyl group which is capable of binding said compound of formula (I) to a molecular recognition unit, selected from

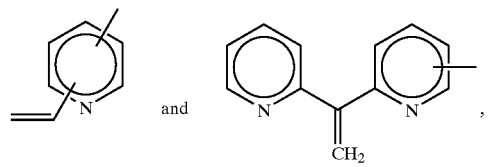

or a pharmaceutically acceptable salt thereof.

2. A compound having the following structure:

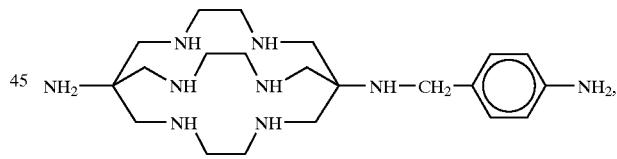

wherein said compound is capable of binding to a molecular recognition unit.

3. A compound according to claim 2 which is complexed with a metal ion.

4. A compound according to claim 2 which is complexed with a metal ion selected from the group consisting of Cu, Tc, Gd, Ga, In, Co, Re, Fe, Au, Ag, Rh, Pt, Bi, Cr, W, Ni, V, Ir, Pt, Zn, Cd, Mn, Ru, Pd, Hg, and Ti.

5. A compound according to claim 4, wherein the metal ion is a radionuclide selected from the group consisting of $^{64}$Cu, $^{67}$Cu, Tc, In, Gd, Ga, Fe, Co, Ti and Re.

6. A compound according to claim 5, wherein the radionuclide is selected from $^{64}$Cu and $^{67}$Cu.

7. A method radioimaging comprising administering to a subject an effective amount of a radiolabelled metal ion complex of a compound, wherein said compound has the structure

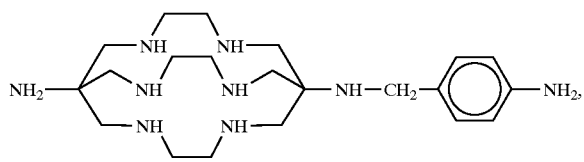

or a pharmaceutically acceptable salt thereof.

8. The method of claim 7, wherein said metal ion is selected from the group consisting of Cu, Tc, Gd, Ga, In, Y Co, Re, Fe, Au, Ag, Rh, Pt, Bi, Cr, W, Ni, V, Ir, Pt, Zn, Cd, Mn, Ru, Pd, Hg, and Ti.

9. The method of claim 8, wherein the metal ion is a radionuclide selected from the group consisting of $^{64}$Cu, $^{67}$Cu, Tc, In, Gd, Ga, Fe, Co, Ti, and Re.

10. The method of claim 9, wherein the radionuclide is selected from $^{64}$Cu and $^{67}$Cu.

11. A compound according to claim 1, wherein the molecular recognition unit is selected from the group consisting of an antibody, protein, peptide, carbohydrate, nucleic acid, oligonucleotide, oligosaccharide and liposome.

12. A compound according to claim 1, wherein W is NH.

13. A compound according to claim 1, wherein said compound is complexed with a metal ion selected from the group consisting of Cu, Tc, Ga, In, Co, Re, Fe, Au, Ag, Rh, Pt, Bi, Cr, W, Ni, V, Pb, Ir, Zn, Cd, Mn, Ru, Pd, Hg, Ti, Y and Sc.

14. A compound according to claim 1, wherein n is 3 or 4 and the compound is complexed with a metal ion is selected from the lanthanide group of elements in the Periodic Table.

15. A compound according to claim 13, wherein the metal ion is selected from the group consisting of Cu, Tc, Gd, Ga, In, Re, Fe, Au, Ag, Rh, Pt, Bi, Cr, W, Ni, V, Pb, Ir, Zn, Cd, Mn, Ru, Pd, Hg, Ti, and Sc.

16. A compound according to claim 13, wherein the metal ion is a radionuclide selected from the group consisting of $^{64}$Cu, $^{67}$Cu, Tc, In, Ga, Fe, Co, Ti, Re, and Y.

17. A compound according to claim 16, wherein the radionuclide is selected from $^{64}$Cu and $^{67}$Cu.

18. A pharmaceutical composition, for radioimaging comprising a compound of Formula (I) compound according to claim 1, a pharmaceutically acceptable salt thereof, or a radiolabelled complex thereof, together with a pharmaceutically acceptable carrier.

19. A diagnostic composition for radiodiagnosis comprising a radiolabelled complex of a compound of Formula (I) according to claim 1, or a pharmaceutically acceptable salt thereof, and a reducing agent, together with a pharmaceutically acceptable carrier.

20. A method of diagnosing cancer comprising administering to a subject an effective amount of a radiolabelled complex of a compound of Formula (I) according to claim 1, or a pharmaceutically acceptable salt thereof, and determining whether or not said subject has the cancer.

21. The method of claim 20, wherein said metal ion is a radionuclide selected from the group consisting of Cu, Tc, Ga, In, Y, Co, Re, Fe, Au, Ag, Rh, Pt, Bi, Cr, W, Ni, V, Pb, Ir, Zn, Cd, Mn, Ru, Pd, Hg, Ti, and Sc.

22. The method of claim 21, wherein the metal ion is a radionuclide selected from the group consisting of $^{64}$Cu, $^{67}$Cu, Tc, In, Ga, Fe, Co, Ti, Re, and Y.

23. The method of claim 22, wherein the radionuclide is selected from $^{64}$Cu and $^{67}$Cu.

24. A method of radioimaging a subject comprising administering to said subject an effective amount of a radiolabelled metal ion complex of a compound of Formula (I) according to claim 1, or a pharmaceutically acceptable salt thereof.

25. A compound according to claim 4, wherein the metal ion is selected from the group consisting of Cu, Tc, Ga, In, Re, Fe, Au, Ag, Rh, Pt, Bi, Cr, W, Ni, V, Ir, Zn, Cd, Mn, Ru, Pd, Hg, and Ti.

26. A pharmaceutical composition comprising a compound according to claim 2, or a pharmaceutically acceptable salt thereof, a metal ion complex thereof, or a radiolabelled complex thereof, together with a pharmaceutically acceptable carrier.

27. A diagnostic composition comprising a radiolabelled metal ion complex of a compound according to claim 2, or a pharmaceutically acceptable salt thereof, and a reducing agent, together with a pharmaceutically acceptable carrier.

28. A compound according to claim 2, wherein the molecular recognition unit is selected from the group consisting of an antibody, protein, peptide, carbohydrate, nucleic acid, oligonucleotide, oligosaccharide and liposome.

29. A compound according to claim 28, wherein the molecular recognition unit is an antibody.

30. A conjugate compound comprising at least one compound of Formula (I) according to claim 1, or a metal complex, or radiolabelled complex, or a pharmaceutically acceptable salt thereof, bonded to at least one molecular recognition unit comprising an antibody, protein, peptide, carbohydrate, oligonucleotide or oligosaccharide.

31. A conjugate compound comprising a compound according to claim 2, or a metal complex, or radiolabelled complex, or a pharmaceutically acceptable salt thereof, bonded to at least one molecular recognition unit comprising an antibody, protein, peptide, carbohydrate, oligonucleotide or oligosaccharide.

32. A compound according to claim 31, wherein the molecular recognition unit is an antibody.

33. A method of radioimaging a subject comprising administering to said subject an effective amount of a radiolabelled metal ion complex of a conjugate compound according to claim 30, or a pharmaceutically acceptable salt thereof.

34. A method of radioimaging a subject comprising administering to said subject an effective amount of a radiolabelled metal ion complex of a conjugate compound according to claim 31, or a pharmaceutically acceptable salt thereof.

35. A pharmaceutical composition comprising a conjugate compound or a metal ion complex thereof according to claim 30, together with a pharmaceutically acceptable carrier.

36. A pharmaceutical composition comprising a conjugate compound or a metal ion complex thereof according to claim 31, together with a pharmaceutically acceptable carrier.

37. A method of radiotherapy of cancer comprising administering to a subject an effective amount of a radiolabelled metal ion complex of a compound, wherein said compound has the structure

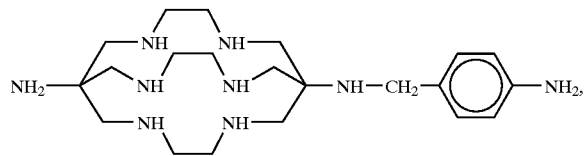

or a pharmaceutically acceptable salt thereof.

38. The method of claim 37, wherein said radiolabelled metal ion is a radionuclide selected from the group consisting of Cu, Ga, In, Co, Re, Fe, Au, Ag, Rh, Pt, Bi, Cr, W, Ni, V, Ir, Zn, Cd, Mn, Ru, Pd, Hg, and Ti.

39. The method of claim 38, wherein the metal ion is a radionuclide selected from the group consisting of $^{64}$Cu, $^{67}$Cu, In, Ga, Fe, Co, Ti, and Re.

40. The method of claim 39, wherein the radionuclide is selected from $^{64}$Cu and $^{67}$Cu.

41. The method of claim 24, wherein said metal ion is a radionuclide selected from the group consisting of Cu, Tc, Ga, In, Y, Co, Re, Fe, Au, Ag, Rh, Pt, Bi, Cr, W, Ni, V, Pb, Ir, Zn, Cd, Mn, Ru, Pd, Hg, Ti, Lu, and Sc.

42. The method of claim 41, wherein said radionuclide is selected from the group consisting of $^{64}$Cu, $^{67}$Cu, Tc, In, Ga, Fe, Co, Ti, Re, Lu and Y.

43. The method of claim 42, wherein the radionuclide is selected from $^{64}$Cu and $^{67}$Cu.

44. A method of radiotherapy of a disease comprising administering to a subject an effective amount of a radiolabelled metal ion complex of a compound of Formula (I) according to claim 1, or a pharmaceutically acceptable salt thereof.

45. The method of claim 44, wherein said metal ion is a radionuclide selected from the group consisting of Cu, Tc, Ga, In, Y, Co, Re, Fe, Au, Ag, Rh, Pt, Bi, Cr, W, Ni, V, Pb, Ir, Pt, Zn, Cd, Mn, Ru, Pd, Hg, Ti, Sc, Sm and Lu.

46. The method of claim 45, wherein the metal ion is a radionuclide selected from the group consisting of $^{64}$Cu, $^{67}$Cu, Tc, In, Ga, Fe, Co, Ti, Re, Sm, Lu and Y.

47. The method of clam 46, wherein the radionuclide is selected from $^{64}$Cu and $^{67}$Cu.

48. The method according to claim 44, wherein n is 3 or 4 and the compound is complexed with a radiolabelled metal ion selected from the lanthanide group of elements in the Periodic Table.

49. A method of radiotherapy of cancer comprising administering to a subject an effective amount of a radiolabelled metal ion complex of a conjugate compound according to claim 30, or pharmaceutically acceptable salt thereof.

50. A method of radiotherapy of cancer comprising administering to a subject an effective amount of a radiolabelled metal ion complex of a conjugate compound according to claim 31, or pharmaceutically acceptable salt thereof.

51. A method of radioimaging cancer comprising administering to a subject an effective amount of a radiolabelled complex of a compound of Formula (I) according to claim 2, or a pharmaceutically acceptable salt thereof.

52. The method of claim 51, wherein said metal ion is a radionuclide selected from the group consisting of Cu, Tc, Ga, In, Co, Re, Fe, Au, Ag, Rh, Pt, Bi, Cr, W, Ni, V, Ir, Zn, Cd, Mn, Ru, Pd, Hg, and Ti.

53. The method of claim 52, wherein the metal ion is a radionuclide selected from the group consisting of $^{64}$Cu, $^{67}$Cu, Tc, In, Ga, Fe, Co, Ti, and Re.

54. The method of claim 53, wherein the radionuclide is selected from $^{64}$Cu and $^{67}$Cu.

55. A method of diagnosing cancer comprising administering to a subject an effective amount of a radiolabelled complex of a compound of Formula (I) according to claim 2, or a pharmaceutically acceptable salt thereof, and determining whether or not the subject has cancer.

56. A method of radiotherapy of cancer comprising administering to a subject an effective amount of a radiolabelled metal ion complex of a compound of Formula (I) according to claim 1, or a pharmaceutically acceptable salt thereof.

57. The method of claim 56, wherein said metal ion is a radionuclide selected from the group consisting of Cu, Ga, In, Y, Co, Re, Fe, Au, Ag, Rh, Pt, Bi, Cr, W, Ni, V, Pb, Ir, Pt, Zn, Cd, Mn, Ru, Pd, Hg, Ti, Sc.

58. The method of claim 57, wherein the metal ion is a radionuclide selected from the group consisting of $^{64}$Cu, $^{67}$Cu, Tc, In, Ga, Fe, Co, Ti, Re, Sm, Lu and Y.

59. The method of claim 58, wherein the radionuclide is selected from $^{64}$Cu and $^{67}$Cu.

* * * * *